United States Patent
Ford et al.

(10) Patent No.: US 8,791,067 B2
(45) Date of Patent: Jul. 29, 2014

(54) METHOD FOR TREATING MALARIA

(75) Inventors: Byron D. Ford, Atlanta, GA (US); Jonathan Stiles, Powder Springs, GA (US); Gregory Ford, Cartersville, GA (US)

(73) Assignee: Morehouse School of Medicine, Atlanta, GA (US)

( * ) Notice: Subject to any disclaimer, the term of this patent is extended or adjusted under 35 U.S.C. 154(b) by 35 days.

(21) Appl. No.: 13/556,847

(22) Filed: Jul. 24, 2012

(65) Prior Publication Data

US 2014/0030251 A1    Jan. 30, 2014

(51) Int. Cl.
*A61K 38/18* (2006.01)
*C07K 14/475* (2006.01)

(52) U.S. Cl.
USPC ............. 514/7.6; 514/1.1; 514/21.2; 530/350

(58) Field of Classification Search
None
See application file for complete search history.

(56) References Cited

U.S. PATENT DOCUMENTS

| | | |
|---|---|---|
| 6,326,507 B1 | 12/2001 | Gribble et al. |
| 6,552,075 B2 | 4/2003 | Gribble et al. |
| 7,435,755 B2 | 10/2008 | Konopleva et al. |
| 2006/0194734 A1 | 8/2006 | Zhou |
| 2010/0120691 A1 | 5/2010 | Ford |
| 2011/0172429 A1 | 7/2011 | Asai et al. |

FOREIGN PATENT DOCUMENTS

WO    2011163466 A1    12/2011

OTHER PUBLICATIONS

Xu, Z. et al., "Extended therapeutic window and functional recovery after intraarterial administration of neuregulin-1 after focal ischemic stroke", Journal of Cerebral Blood Flow & Metabolism, pp. 527-535, vol. 26, published online Aug. 2005.
Scharf, K. D. et al., "6 Heat stress promoters and transcription factors", Results and Probl. Cell Differ., 1994, pp. 125-162, vol. 20.
Bitter, G. A. et al., "Expression and Secretion Vectors for Yeast", Methods in Enzymology, 1987, pp. 516-544, vol. 153.
Croslan, D. R. et al., "Neuroprotective effects of Neuregulin-1 on B35 Neuronal Cells following Ischemia", Brain Res., May 19, 2008, vol. 1210, pp. 39-47.
International Search Report and Written Opinion of the International Searching Authority of International Application No. PCT/US2012/047981 mailed Dec. 27, 2012.

*Primary Examiner* — Christine J Saoud
*Assistant Examiner* — Jon M Lockard
(74) *Attorney, Agent, or Firm* — Ping Wang; Andrews Kurth LLP

(57) ABSTRACT

Compositions and methods for preventing or ameliorating tissue damage caused by an inflammatory disorder or pathogenic infections are described. In one aspect, a method for preventing or ameliorating tissue damage caused by an inflammatory disorder or pathogenic infection comprises administering to a subject a therapeutically effective amount of a neuregulin. In another aspect, the composition comprises one or more active agents that: (a) increase expression or activity of a neuregulin; (b) inhibit the expression or activity of CXCL10, STAT3 or HEME; or (c) both (a) and (b).

12 Claims, 14 Drawing Sheets

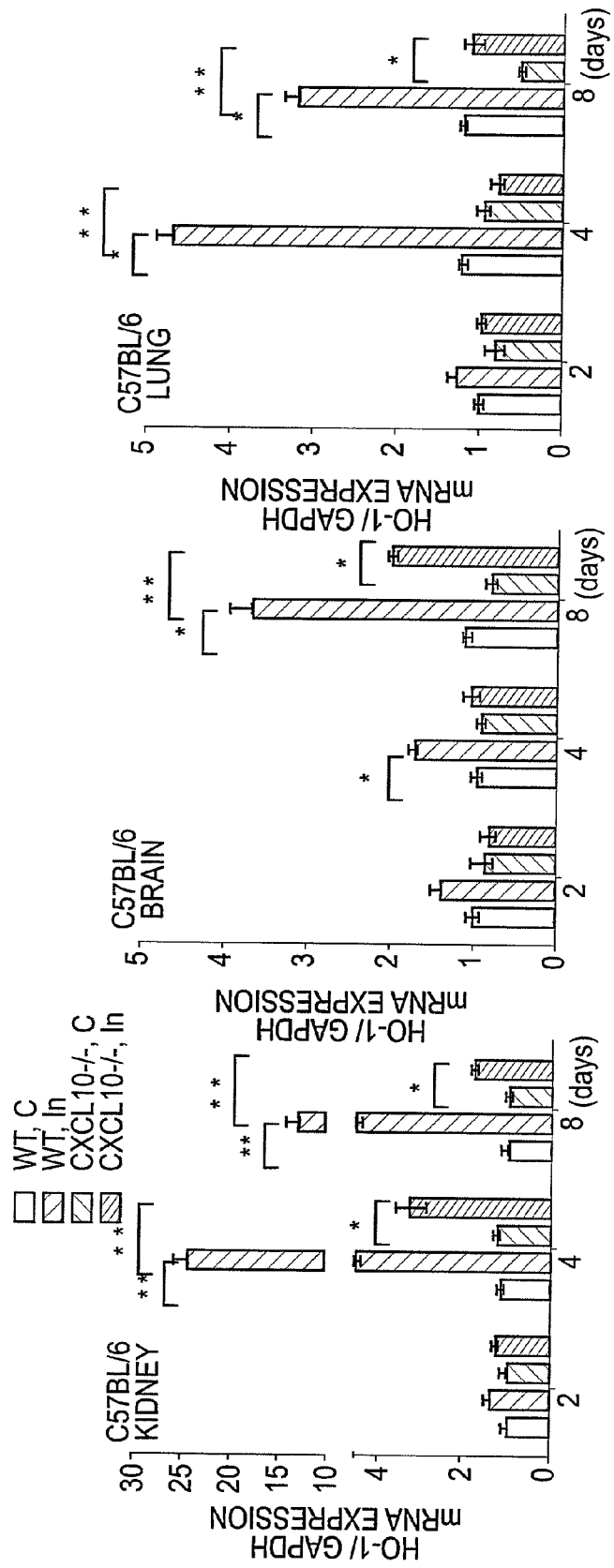

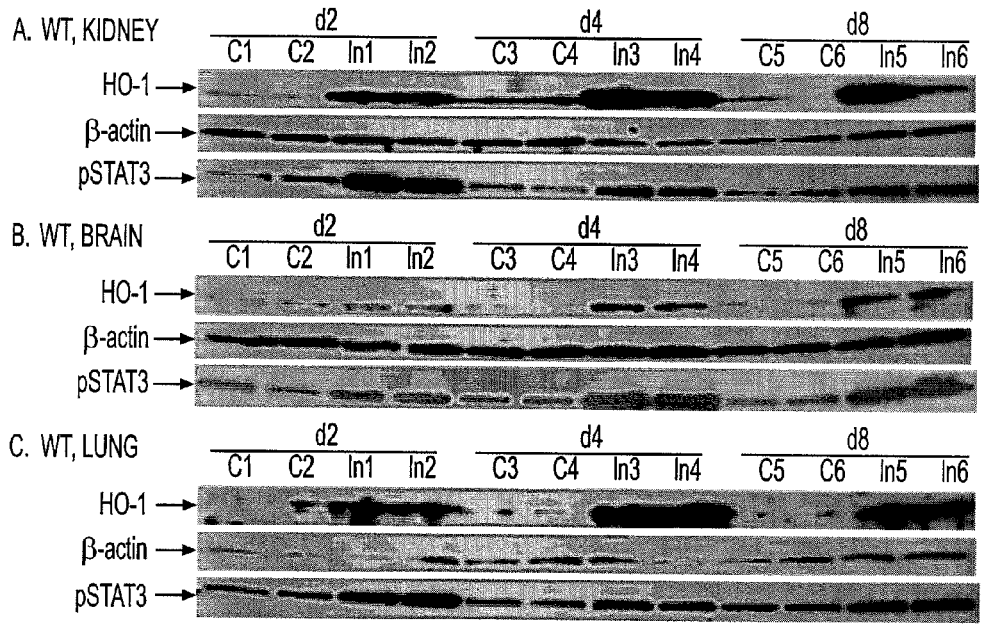
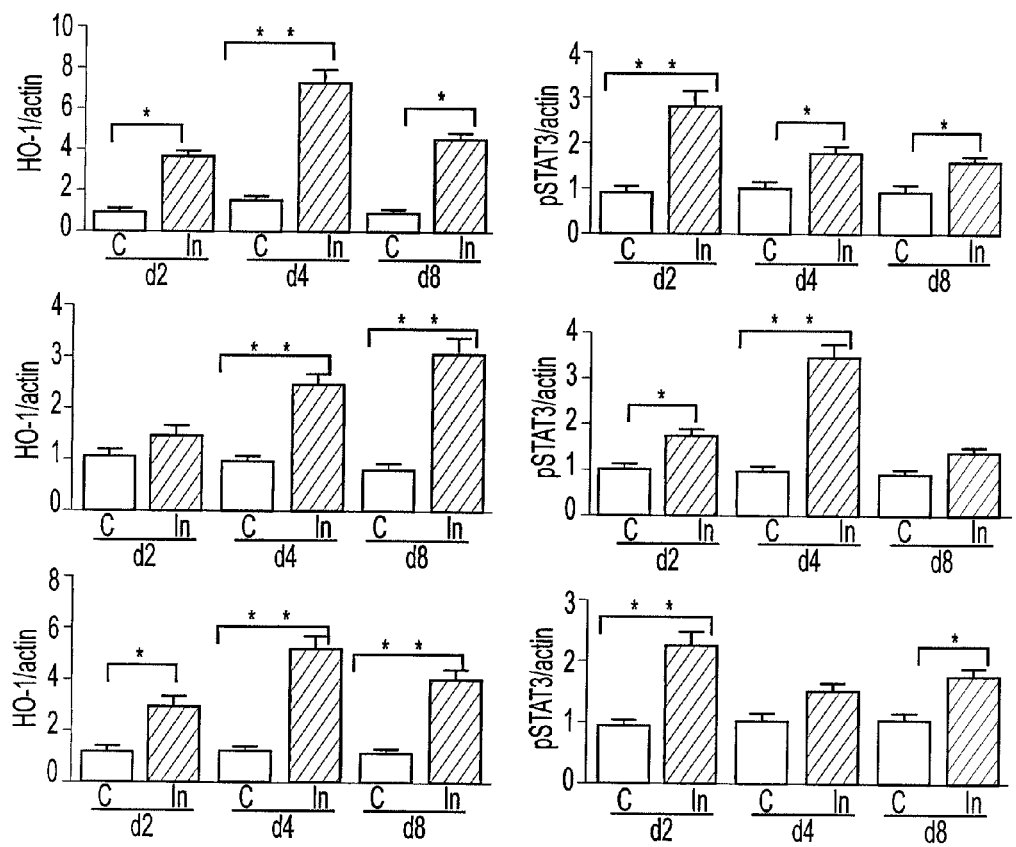
FIG. 3

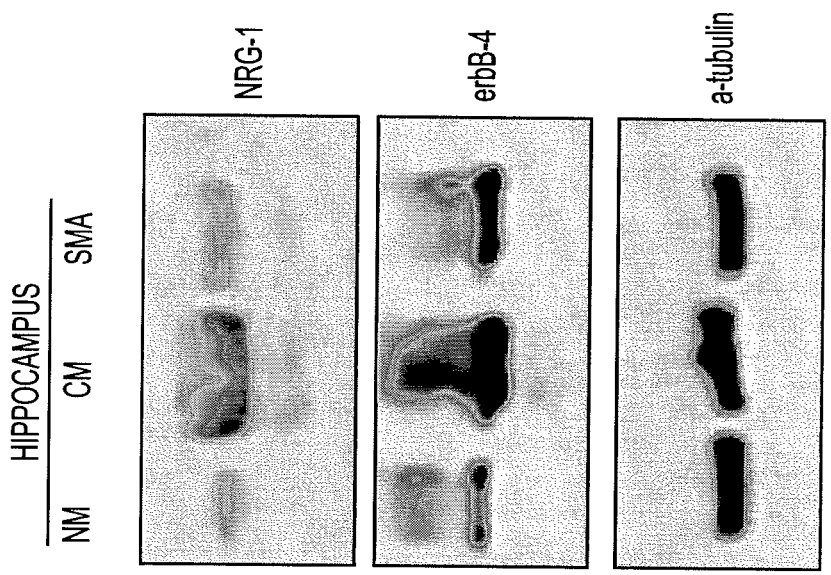
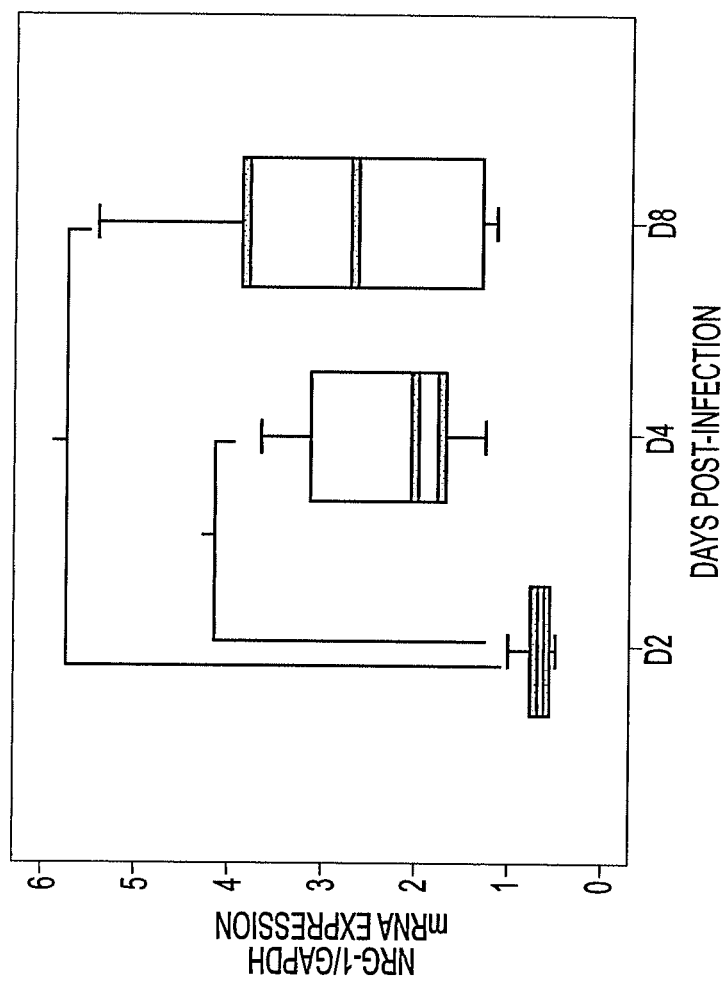
FIG. 5B
FIG. 5A

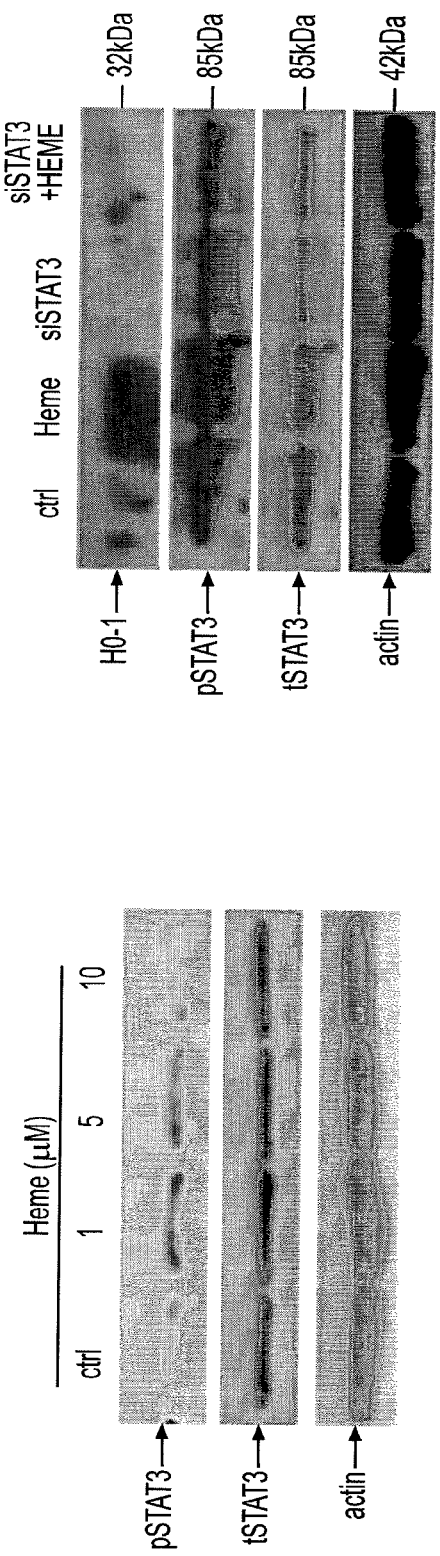
FIG. 6B
FIG. 6A
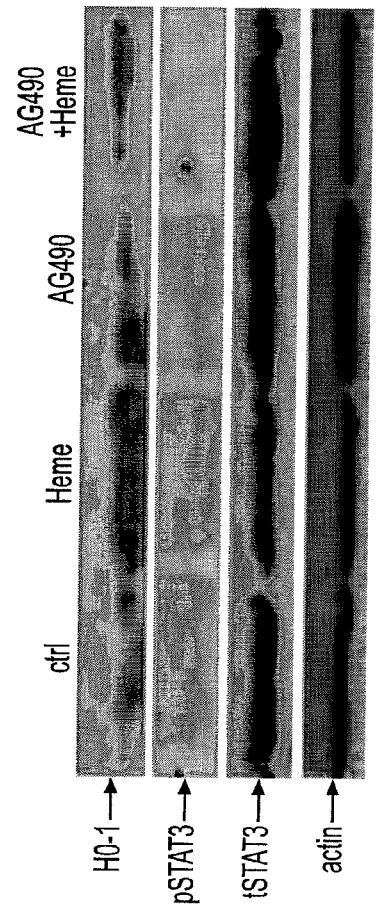
FIG. 6C

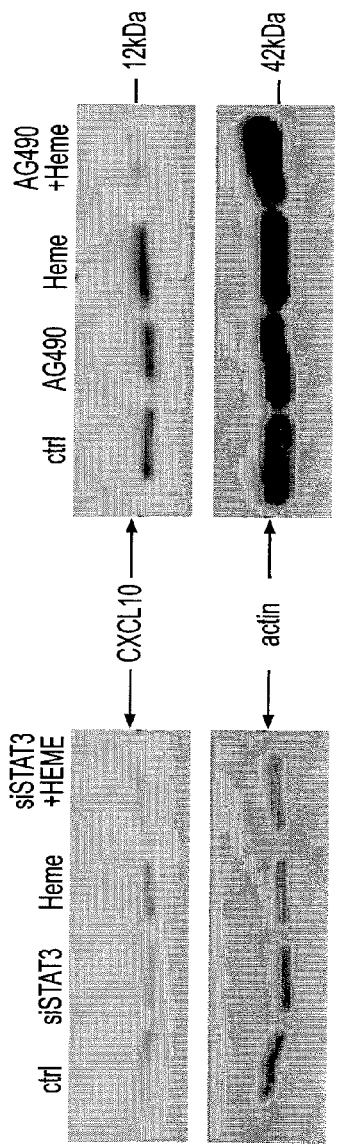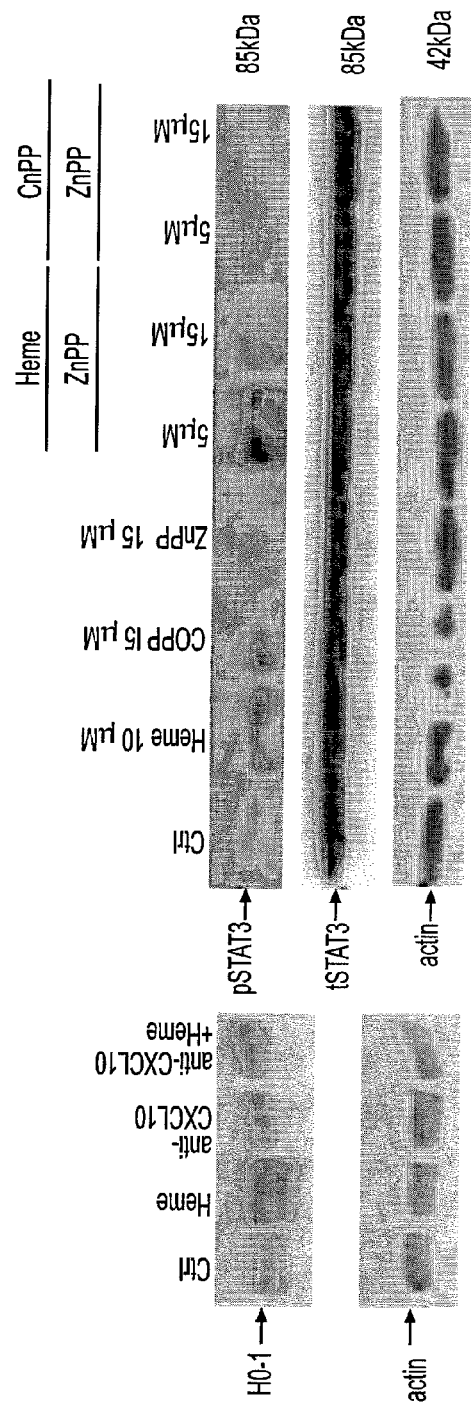
FIG. 6D  FIG. 6E  FIG. 6F  FIG. 6G

| POSITION | GENE SYMBOL | FOLD REGULATION |
| --- | --- | --- |
| A06 | CEBPB | 2.2411 |
| B06 | FCGR1A | 2.0745 |
| D05 | JUN8 | 2.2056 |
| D06 | MMP3 | 8.4786 |
| D09 | NFKB1 | 4.6969 |
| F07 | SOCS3 | 2.0337 |
| F08 | SOCS4 | 2.1574 |
| G05 | STAT4 | 2.0055 |
| B03 | F2R | -2.6314 |
| D12 | OAS1 | -4.1302 |

*FIG. 8*

METHOD FOR TREATING MALARIA

FIELD

This application relates generally to compositions containing a neuregulin for prevention and treatment of neuronal and vascular damage resulting from various inflammatory disorders or pathogenic infections.

BACKGROUND

Malaria, which is caused by *Plasmodium falciparum*, infects 200 to 300 million people globally and kills 900,000 (mostly children) every year. Severe malaria-related pathogenesis impacts a broad spectrum of systems and multiple organs. Up to 20% of fatal cases are due to cerebral malaria (CM) and other severe forms of malaria such as severe malaria anemia (SMA). Although the cause of fatal CM is not fully understood, accumulating evidence suggests that complications linked to tissue injury in brain, lung (acute lung injury (ALI), acute respiratory distress syndrome (ARDS)) and kidney (acute renal failure) resulting from malaria contributes to the high morbidity and mortality associated with the disease.

Severe malaria is associated with perturbation of inflammatory cytokines, chemokines, anti-inflammatory cytokines, angiopoietic factors and signalling pathways. Recently, it has been shown that increased level of free HEME produced during malaria infection induces inflammation that damages host vascular endothelium which is responsible for induction of fatal cerebral pathogenesis, as well as ALI and ARDS. HEME oxygenase (HO) is the rate-limiting step enzyme in the degradation of HEME groups to biliverdin, carbon monoxide (CO) and iron.

Despite the availability of treatments for malaria, the mortality associated with severe malaria (e.g., CM, SMA and ARDS) remains high. Most adjunct treatments have not improved the number of fatal outcomes, since these treatments focus mainly on the clearance of parasites in acute disease and not deleterious secondary parasites and host factors that may appear early in infection or remain after treatment. Accordingly, there remains a need for therapeutic approaches for preventing or ameliorating tissue damage caused by malarial infections, as well as other inflammatory disorders and pathogenic infections.

Neuregulin-1 (NRG-1) is a family of growth factors known to effectively attenuate pathology and tissue damage associated with neurodegenerative disorders such as acute ischemic stroke (AIS) and neurotoxin exposure. Neuroprotection from NRG-1 involves inhibition of apoptotic and proinflammatory pathways in target cells such as neuroglial cells. Thus, by inhibiting tissue damage NRG-1 lengthens the therapeutic window in murine AIS models. CM pathogenesis shares some fundamental similarities with both TBI and AIS in occlusion of vessels, glial activation, focal inflammation, activation of apoptotic pathways and reversible and irreversible neuronal tissue damage.

SUMMARY

One aspect of the present invention relates to a method for preventing or ameliorating tissue damage caused by an inflammatory disorder or pathogenic infection in a subject, comprising administering to a subject in need of such treatment a composition comprising a therapeutically effective amount of a neuregulin, wherein the neuregulin is administered in a dosage range from about 0.01 mg/kg body weight/day to about 1000 mg/kg body weight/day.

In another aspect, a method for preventing or ameliorating tissue damage caused by an inflammatory disorder or pathogenic infection in a subject, comprises administering to the subject therapeutically effective amount(s) of one or more active agents that: (a) increase expression or activity of a neuregulin; (b) inhibit the expression or activity of CXCL10, STAT3 or HEME; or (c) both (a) and (b).

In a further aspect, a method for enhancing the effect of anti-inflammatory therapy, comprises administering to a subject who is receiving or has received anti-inflammatory therapy an effective amount of a neuregulin, wherein the neuregulin is administered in a dosage range from about 0.01 mg/kg body weight/day to about 1000 mg/kg body weight/day.

In some embodiments, the inflammatory disorder or pathogenic infection is characterized by elevated expression or activity of CXCL10, STAT3 and/or HEME.

In some embodiments, the neuregulin is administered in conjunction with a secondary active agent. In some embodiments, the secondary active agent is a HEME neutralization agent, a CXCL10 inhibitor, a CXCR3 inhibitor, a STAT3 inhibitor, an anti-inflammatory agent, an antimicrobial agent or combination thereof. In other embodiments, the secondary active agent is administered in a dosage range from about 0.01 mg/kg body weight/day to about 1000 mg/kg body weight/day.

In a particular embodiment, the secondary active agent is a HEME neutralization agent selected from the group consisting of HEME oxygenase, HEME oxygenase activators, heavy metal salts, such as cadmium chloride and cobalt chloride, clotrimazole, miconazole, ketoconazole, rhein, diacerhein, including derivatives and combinations therefrom.

In another embodiment, the secondary active agent comprises an antibody, short interfering RNA (siRNA), aptamer, synbody, target neutralization agent, peptide, aptamer-siRNA chimera, single stranded antisense oligonucleotide, triplex forming oligonucleotide, ribozyme, external guide sequence or antagonist encoded expression vector.

In another aspect, a pharmaceutical composition for use in the above-described methods comprises a neuregulin; a secondary active agent selected from the group consisting of HEME neutralization agent, CXCL10 inhibitor, CXCR3 inhibitor, STAT3 inhibitor, anti-inflammatory agent, antimicrobial agent and combination thereof; and a pharmaceutically acceptable carrier. In a related aspect, a method for preventing or ameliorating tissue damage caused by an inflammatory disorder or pathogenic infection in a subject, comprises administering into a subject in need of such treatment an effective amount of the pharmaceutical composition.

In one embodiment, the inflammatory disorder or pathogenic infection is an inflammatory disease of the central or peripheral nervous system selected from the group consisting of abscess, AIDS related infections, Alzheimer's disease, chronic fatigue syndrome, congenital infections, encephalitis, ischemia/stroke, meningitis, migraine, multiple sclerosis and traumatic brain injury.

In another embodiment, the inflammatory disorder or pathogenic infection is an inflammatory disease or infection of the urogenital system selected from the group consisting of endometriosis, glomerulosclerosis, infections of the vagina and cervix, intra-amniotic infection, pelvic inflammatory disease, renal inflammation/nephritis, sexually transmitted diseases, urethritis, urinary tract infections and yeast infections.

In another embodiment, the inflammatory disorder or pathogenic infection is an inflammatory disease or infection of the digestive system selected from the group consisting of colon cancer, hepatitis, inflammatory bowel disease, interstitial cystitis, irritable bowel syndrome and ulcers.

In another embodiment, the inflammatory disorder or pathogenic infection is an inflammatory disease or infection of the respiratory system selected from the group consisting of chronic lung disease, asthma, tuberculosis and pneumonia.

In another embodiment, the inflammatory disorder or pathogenic infection is an inflammatory disease of the skin, integument and/or musculoskeletal system selected from the group consisting of Behcet's Disease, Crohn's disease, dermatitis, gingivitis, gout, myalgia, osteoarthritis, periodontitis, psoriasis, rheumatoid arthritis, spondyloarthropathies and skin sunburn.

In another embodiment, the inflammatory disorder or pathogenic infection is an inflammatory disease or infection of the cardiovascular system selected from the group consisting of atherosclerosis, pericarditis, endocarditis, Kawasaki's Disease, myocarditis, rheumatic fever and vasculitis.

In another embodiment, the inflammatory disorder or pathogenic infection is an inflammatory disease selected from the group consisting of autoimmune disease or, cat scratch disease, eye infections, Lyme disease, lymphadenopathy, lymphatic inflammation, opportunistic infections, radiation-induced inflammation, sarcoidosis, Sjogren's syndrome and systemic lupus erythematosus and related disorders.

In another embodiment, the inflammatory disorder or pathogenic infection is a pathogenic infection caused by an infectious agent or corresponding disease selected from the group consisting of bacterial infections, sepsis, fungal infections, parasitic infections, cerebral malaria, prion protein infections, toxic compounds, nerve agents and viral infections.

Another aspect of the present application relates to a method for preventing or ameliorating secondary tissue damage caused by an inflammatory disorder or pathogenic infection in a subject. The method comprises: administering into a subject in need of such treatment an effective amount of a neuregulin. In one embodiment, the method further comprises: administering into the subject a secondary active agent selected from the group consisting of HEME neutralization agent, CXCL10 inhibitor, CXCR3 inhibitor, STAT3 inhibitor, anti-inflammatory agent, antimicrobial agent and combinations thereof.

Another aspect of the present application relates to a method for reducing mortality caused by the secondary effect of a pathogenic infection in a subject. The method comprises: administering into a subject in need of such treatment an effective amount of a neuregulin. In one embodiment, the method further comprises administering into the subject a secondary active agent selected from the group consisting of HEME neutralization agent, CXCL10 inhibitor, CXCR3 inhibitor, STAT3 inhibitor, anti-inflammatory agent, antimicrobial agent and combinations thereof. In another embodiment, the pathogen infection is cerebral malaria.

BRIEF DESCRIPTION OF THE DRAWINGS

The invention of this application is better understood in conjunction with the following drawing, in which:

FIG. 2 shows the mean ratio of Hmox1 (HO-1) mRNA expression to GAPDH expression in kidney (A), brain (B) and lung (C) tissues of mice infected with PBA.

FIG. 5A shows the mean ratio of Neuregulin-1 (NRG-1) mRNA expression to GAPDH expression at 2, 4 and 8 days post-infection with PBA. FIG. 5B shows NRG-1 protein expression in post mortem human brain tissues. NM: no malaria; CM: cerebral malaria; SMA: severe anemia malaria.

FIG. 6 shows the effects of in vitro treatment of the mouse brain endothelial cell line CRL2581 with HEME, short interfering STAT3 (siSTAT3), AG490, CoPP and ZnPP. FIG. 6A shows phospho-STAT3 (pSTAT3) and total STAT3 (tSTAT3) protein levels at increasing levels of HEME. FIG. 6B shows protein expression of HO-1, pSTAT3 and tSTAT3 relative to actin in untreated control (ctrl) CRL-2581 cells and in cells treated with HEME, short interfering STAT3 (siSTAT3) and siSTAT3+HEME. FIG. 6C additionally shows protein expression of HO-1, pSTAT3 and tSTAT3 relative to actin following treatment of cells with AG490, a Jak/STAT3 inhibitor and AG490+HEME. FIGS. 6D and 6E show protein expression of CXCL10 relative to actin in untreated control cells (D, E) and in cells treated with siSTAT3 (D), HEME (D, E), siSTAT3+HEME (D), AG490 (E) or AG490+HEME (E). FIG. 6F shows protein expression of HO-1 relative to actin in untreated control cells and in cells treated with HEME, anti-CXCL10 antibody (Ab) or anti-CXCL10 Ab+HEME. FIG. 6G shows protein expression of pSTAT3 and tSTAT3 relative to actin in untreated control cells and in cells treated with HEME, CoPP, ZnPP, HEME+ZnPP or CoPP+ZnPP.

FIG. 8 shows target genes of the JAK2/STAT3 pathway induced by treatment of HBVEC cells with HEME.

DETAILED DESCRIPTION

Figure 1A:
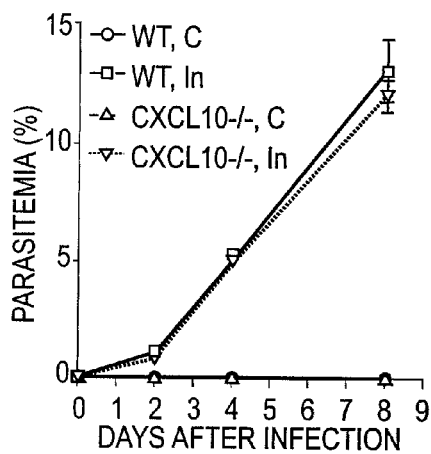
FIG. 1A is a graph showing incidence of parasitemia following intraperitoneal inoculation of both wild-type (WT) and CXCL10-/- C57BL/6 mice with $1 \times 10^6$ P. berghei ANKA (PBA) parasitized red blood cells (infected RBCs, iRBCs) or with non-infected control (C) RBCs.
Figure 1B:
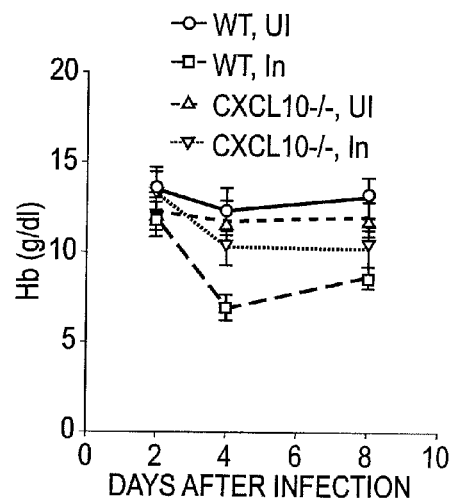
FIG. 1B is a graph showing hemoglobin levels in the mice depicted in FIG. 1A.
Figure 1C:
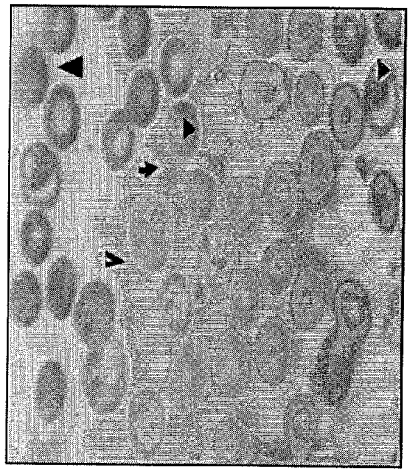
FIGS. 1C and 1D show blood smears illustrating similar maturation stages of the parasite in WT (FIG. 1C) and CXCL10 gene deficient (CXCL10-/-) mice (FIG. 1D).
Figure 1D:
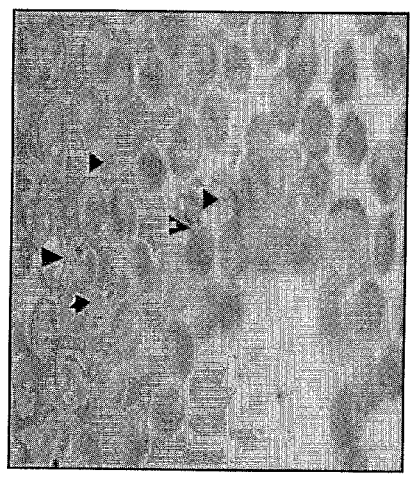
Figure 1E:
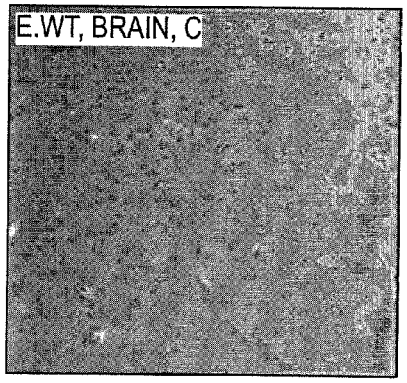
FIGS. 1E and 1F show histopathologic sections from brain tissues obtained from non-infected mice (FIG. 1E) and from infected mice (FIG. 1F) with experimental cerebral malaria (ECM).
Figure 1F:
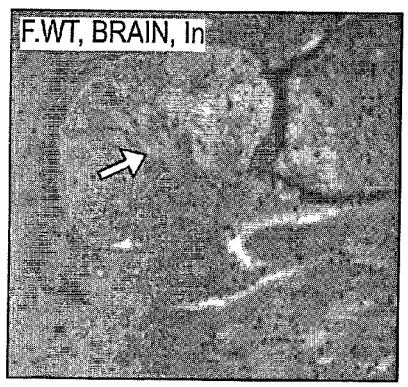
Figure 1G:
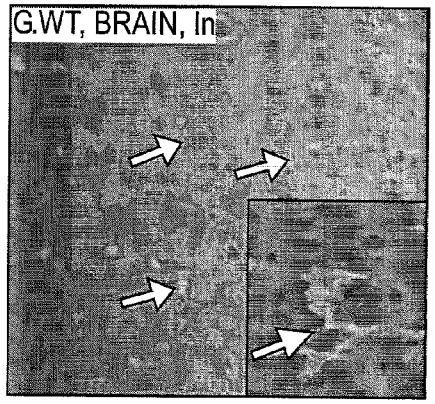
FIGS. 1G, 1H (brain), 1K, 1L (lung) and 1O, 1P (kidney) show pathologic lesions from brain tissues of infected WT mice with ECM.
Figure 1H:
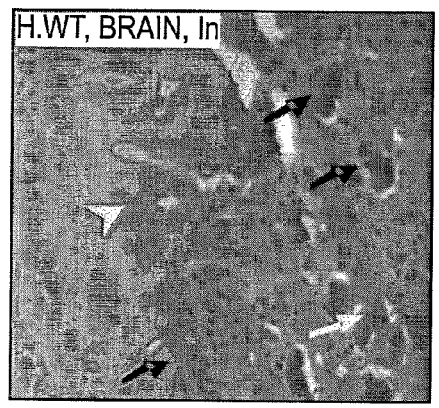
Figure 1I:
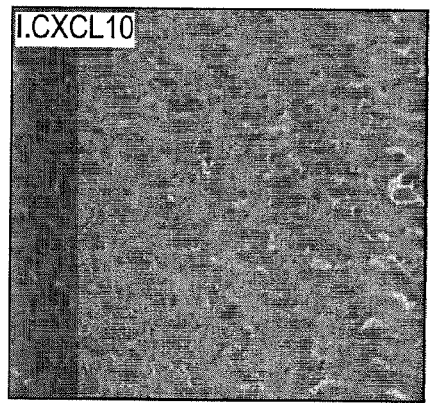
FIGS. 1I, 1J (brain), 1M, 1N (lung) and 1Q, 1R (lung) show no obvious lesions in infected CXCL10 gene deficient (CXCL10-/-) mice.
Figure 1J:
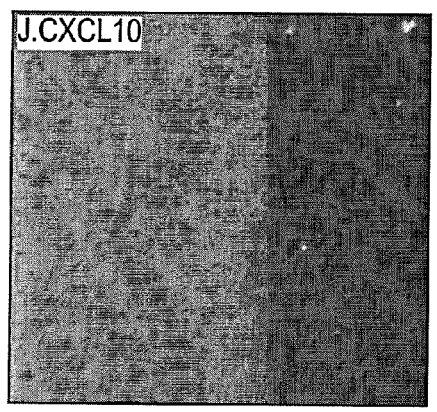
Figure 1K:
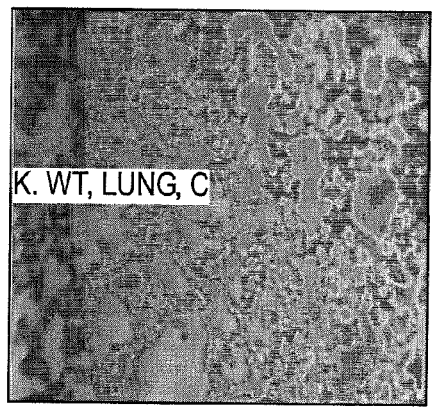
FIG. 1S is a section from pulmonary and tissues and blood vessels showing strong von Willebrand factor (vWF)-positive cells.
FIG. 1T is a TUNEL assay showing apoptotic cells from the section in FIG. 1S.
FIG. 1U is a merged image of FIGS. 1S and 1T showing co-localization of vWF-positive and TUNEL-positive cells in lung, confirming the presence of apoptotic pulmonary endothelial cells.
FIGS. 1V (anti-vWF), 1W (TUNEL) and 1X (merged) show no apoptotic pulmonary endothelial cells in non-infected control mice.
Figure 1L:
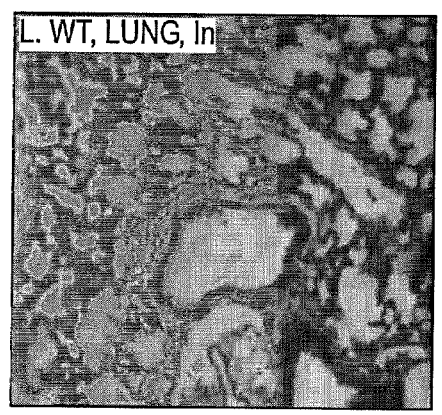
Figure 1M:
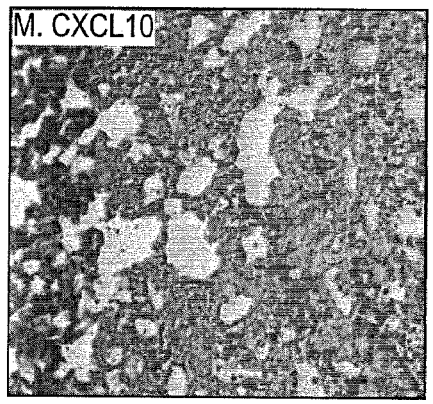
Figure 1N:
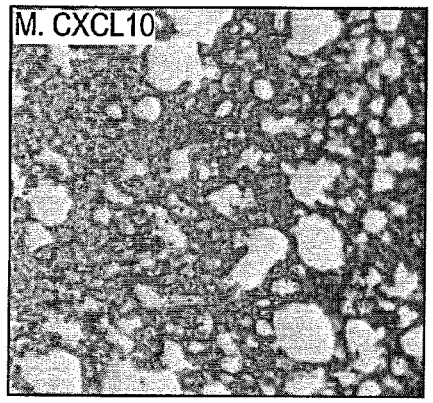
Figure 1O:
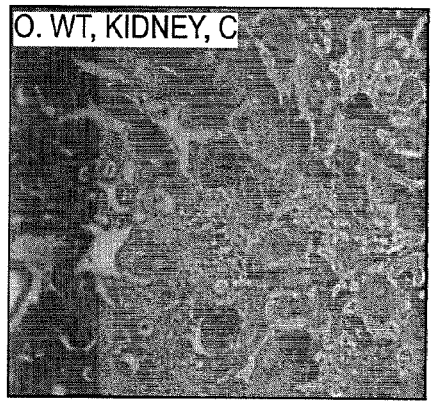
Figure 1P:
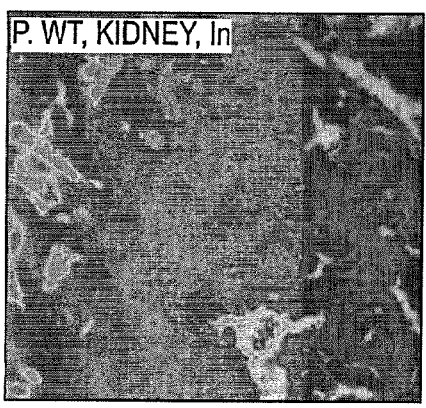
Figure 1Q:
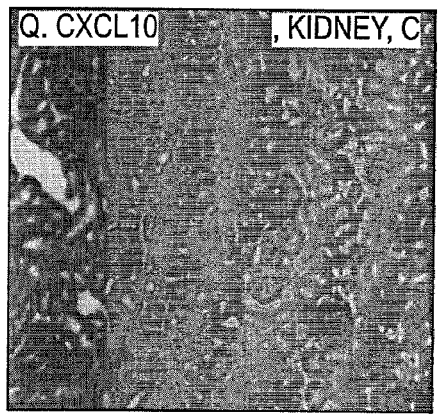
Figure 1R:
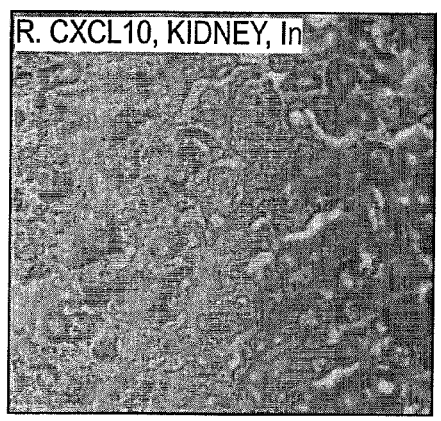
Figure 1S:
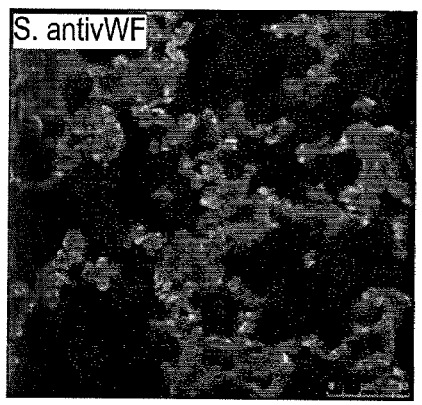
Figure 1T:
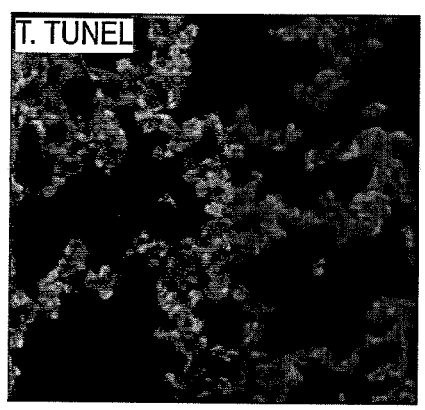
Figure 1U:
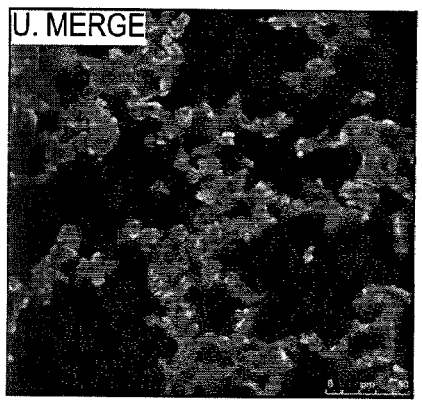

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Definitions

Unless otherwise defined, scientific and technical terms used in connection with the present invention shall have the meanings that are commonly understood by those of ordinary skill in the art.

As used in the specification and the appended claims, the singular forms "a," "an" and "the" include plural referents unless the context clearly dictates otherwise. Thus, for example, reference to "a pharmaceutical carrier" includes mixtures of two or more such carriers and the like.

The term "neuregulin" as used herein, refers to a family of proteins that includes: neuregulin-1 (NRG1), neuregulin-2 (NRG2), neuregulin-3 (NRG3), and neuregulin-4 (NRG4). Neuregulin-1, which has also been described in the literature as acetylcholine receptor inducing activity (ARIA), glial growth factor (GGF), glial growth factor 2 (GGF2); heregulin and neu differentiation factor (NDF); sensory and motor neuron-derived factor (SMDF), HGL; HRG; HRG1; HRGA and MST131, further contains a number of isoforms that include type I NRG1, type II NRG1, type III NRG1, type IV NRG1, type V NRG1 and type VI NRG1. The term "NRG1," as used herein, also includes all other NRG1 isoforms. NRG1 isoforms are synthesized as transmembrane precursors consisting of either an immunoglobulin-like or cysteine-rich domain, an EGF-like domain, a transmembrane domain and a cytoplasmic tail and are generated from one gene by alternative mRNA splicing and most of them are synthesized as part of a larger transmembrane precursor. The two major classes of NRG1 include α and β isoforms. The NRG1β isoforms predominate in the nervous system, while a isoforms are prevalent in mesenchymal cells. The effects of NRG1 appear to be mediated by interaction with a class of tyrosine kinase receptors related to the epidermal growth factor (EGF) receptor, which includes erbB2, erbB3 and erbB4.

Neuregulin 2 (NRG2) is another member of the neuregulin family of growth and differentiation factors. NRG2 interacts with the ErbB family of receptors and induces the growth and differentiation of epithelial, neuronal, glial and other types of cells. NRG 1 and NRG2 mediate distinct biological processes by acting at different sites in tissues and eliciting different biological responses in cells.

Neuregulin 3 (NRG3) binds to the extracellular domain of the ERBB4 receptor tyrosine kinase but not to the related family members ERBB2 or ERBB3. NRG3 binding stimulates tyrosine phosphorylation of ERBB4.

Neuregulin 4 (NRG4) activates type-1 growth factor receptors (EGFR) to initiating cell-to-cell signaling through tyrosine phosphorylation. Loss of expression of NRG4 is frequently seen in advanced bladder cancer while increased NRG4 expression correlates with better survival.

Any one of the above-described neuregulins may be used in the practice of the present invention. Examples of human neuregulin sequences include, but are not limited to, those listed under GenBank Accession NOs: ADN85612.1, AAF28851.1, AAF28850.1, AAF28849.1, AAF28848.1, ABR13844.1, ABR13843.1, EAW63417.1, EAW63416.1, EAW63415.1, AAI50610.1, ABQ53540.1, DAA00042.1, DAA00041.1, EAW62087.1, EAW62086.1, EAW62085.1, EAW62084.1, EAW62082.1, EAW62081.1, ADK90032.1, ADK90031.1, ADK90030.1, ADK90029.1, ADK90026.1, ADK90024.1, ADK90022.1, AAF28853.1, AAF28852.1, BAG70289.1, BAG70145.1, ABR13842.1, ABG77979.1, DAA00045.1, EAW63419.1, EAW63412.1, EAW63410.1, EAW63409.1, EAW63408.1, ADN85613.1, AAI36812.1, ABQ53539.1, DAA00048.1, DAA00047.1, EAW62083.1, EAW62078.1, ADK90028.1, ADK90027.1, ADK90025.1, ADK90023.1, ADK90021.1, ADK90020.1, AAH73871.1, ABY66350.1, EAW99228.1, EAW99227.1, EAW62080.1, EAW62079.1, EAW63418.1, EAW63414.1, EAW63413.1, EAW63411.1, EAW63407.1, EAW80374.1, AAH64587.1, AAH06492.1, AAO49724.1, AAH07675.1, AAP36053.1, AAH17568.1, CAI15622.1, CAH73645.1, CAH70641.1, CAI17213.1, CAH71050.1, AAM71141.1, AAM71140.1, AAM71139.1, AAM71138.1, AAM71137.1, AAM71136.1, AAM71135.1, AAM71134.1, AAM71133.1, CAI22410.1, ABQ53543.1, ABQ53542.1, ABQ53541.1, DAA00046.1, DAA00044.1, DAA00043.1, DAA00040.1, CAL35830.1, CAL35831.1, CAL35829.1, BAD97155.1, NP_001159445.1, NP_001159444.1, NP_001010848.2, NP_004874.1, NP_053585.1, NP_001171864.1, NP_053586.1, NP_053584.1, Q02297.3, NP_001153467.1, NP_039258.1, NP_039251.2, NP_001153473.1, NP_001153471.1, NP_039250.2, NP_001153476.1, NP_612640.1, NP_039254.1, NP_001153468.1, NP_039256.2, NP_001153480.1, O14511.1, Q9H013.3, Q7RTV8, NP_039252.2, NP_001153479.1, NP_001153474.1, NP_001153477.1, NP_004486.2, NP_039253.1, P56975.1, AAA19954.1, AAA19953.1, AAA19951.1, AAA19950.1, AAB59358.1; AAB59622.1; AAI03985.2, AAI03985.2, AAI14335.2, AAI03984.2, Q8WWG1.1, AAA58640.1, AAA58639.1, AAA58638.1, AAC51756.1, AAY17216.1, 1910316A, ABY70644.1, ABY66349.1, ABY66348.1, ABC69293.1, AAA19952.1; AAA19955.1; AAA58641.1; AAB59358.1; AAB59622.1; AAC41764.1; AAH73871.1; AAI14334.2; AAI36812.1; AAO49724.1; AAP36053.1; ABC69293.1; ABQ53539.1; ABQ53540.1; ABR13843.1; ABR18344.1; ABY66350.1; BAA23417.1; BAD97155.1; BAF83419.1; BAF82616.1; BAG54044.1; BAG53780.1; BAG59183.1; BAH11473.1; BAH11479.1; BAH12729.1; CAD98015.1; CAG29284.1; CAH18333.1.

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

The term "inhibits" is a relative term, an agent inhibits a response or condition if the response or condition is quantitatively diminished following administration of the agent or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an inflammatory response, can, but does not necessarily completely eliminate such a response, so long as the response is measurably diminished, for example, by at least about 50%, such as by at least about 70% or about 80% or even by about 90% of (that is to 10% or less than) the response in the absence of the agent or in comparison to a reference agent.

As used herein, the phrase "preventing or ameliorating tissue damage" refers to a reduction or prevention of tissue damage manifested in tissues affected by an inflammatory disorder or pathogenic infection, such as *P. falciparum*.

As used herein, the term "secondary active agent" refers to a biologic agent which contributes to preventing or ameliorating tissue damage caused by inflammatory disorders or pathogenic infections. The active agent may work additively or synergistically with the neuregulin to ameliorate or prevent tissue damage caused by inflammatory disorders or pathogenic infections. Exemplary active agents include antibodies, antibody fragments, short interfering RNAs (siRNAs), aptamers, synbodies, target neutralization agents, peptides, aptamer-siRNA chimeras, single stranded antisense oligonucleotides, triplex forming oligonucleotides, ribozymes, external guide sequences, anti-inflammatory agents, antimicrobial agent, agent-encoding expression vectors and the like.

As used herein, the term "antibody" refers to immunoglobulin molecules and immunologically active portions of immunoglobulin (Ig) molecules, i.e., molecules that contain an antigen binding site or epitope binding domain that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies) and antibody fragments so long as they exhibit specific binding to a target antigen. By "specifically bind" or "immunoreacts with" is meant that the antibody reacts with one or more antigenic determinants of the desired antigen and does not react (i.e., bind) with other polypeptides or binds at much lower affinity with other polypeptides. The term "antibody" also includes antibody fragments that comprise a portion of a full length antibody, generally the antigen binding or variable region thereof.

As used herein, the term "nucleic acid" refers to a polydeoxyribonucleotide (DNA or an analog thereof) or polyribonucleotide (RNA or an analog thereof) made up of at least two and preferably ten or more bases linked by a backbone structure. Exemplary nucleic acids include single-stranded (ss), double-stranded (ds) or triple-stranded polynucleotides or oligonucleotides of DNA and RNA.

The term "polynucleotide" refers to nucleic acids containing more than 10 nucleotides.

The term "oligonucleotide" refers to a single stranded nucleic acid containing between about 5 to about 100 nucleotides.

In a pharmacological sense, in the context of the present invention, a "therapeutically effective amount" of a neuregulin, secondary active agent or combination thereof refers to an amount effective in the prevention or treatment of a disorder for the treatment of which the active agent or combination thereof is effective. A "disorder" or "disease" is any inflammation associated disorder or pathogenic invention that would benefit from treatment with the neuregulin and/or secondary active agent.

Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint and independently of the other endpoint.

The term "pathogenic infection" refers to the invasion of body tissues by disease-causing microorganisms, their multiplication and the reaction of body tissues to these microorganisms and the toxins that they produce. "Pathogenic infection" includes but are not limited to infections by viruses, prions, bacteria, viroids, parasites, protozoans and fungi.

The term "the secondary effect of a pathogenic infection" or "the secondary tissue damage caused by an inflammatory disorder or pathogenic infection" refers to the effect or tissue damage caused by cytotoxic factors secondary to an inflammatory disorder or pathogenic infection. Examples of such cytotoxic factors include, but are not limited to, Heme, HO-1, CXCL10, CXCR3 and STAT3.

It is also understood that there are a number of values disclosed herein and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

Methods for Treating Inflammatory Disorders or Pathogenic Infections

The present application challenges the traditional concept of treating pathogenic infections, such as malaria, which targets pathogen clearance from peripheral blood in acute symptomatic cases and provides a preventive approach that targets early biomarkers and signals of fatal disease while depleting cytotoxic factors secondary to pathogenic infection. The present application further provides a therapeutic approach for targeting common biological targets associated with other pathogenic infections and inflammatory disorders by preventing or ameliorating tissue damage caused by these infections or disorders.

One aspect of the present invention relates for treating inflammatory disorders or pathogenic infections. In one embodiment, a method for preventing or ameliorating tissue damage caused by an inflammatory disorder or pathogenic infection in a subject comprises administering to a subject in need of such treatment a composition comprising a therapeutically effective amount of a neuregulin.

In another embodiment, a method for preventing or ameliorating tissue damage caused by an inflammatory disorder or pathogenic infection in a subject comprises administering to the subject therapeutically effective amount(s) of one or more biological agents that: (a) increase expression or activity of a neuregulin; (b) inhibit the expression or activity of CXCL10, STAT3 or HEME; or (c) both (a) and (b).

In yet another embodiment, a method for enhancing treatment of an inflammatory disorder or pathogenic infection comprises administering to a subject who is receiving or has received treatment therefor an effective amount of a neuregulin.

Another aspect of the present application relates to a method for preventing or ameliorating secondary tissue damage caused by an inflammatory disorder or pathogenic infection in a subject. The method comprises: administering into a subject in need of such treatment an effective amount of a neuregulin. In one embodiment, the method further comprises: administering into the subject a secondary active agent selected from the group consisting of HEME neutralization agent, CXCL10 inhibitor, CXCR3 inhibitor, STAT3 inhibitor, anti-inflammatory agent, antimicrobial agent and combinations thereof.

Another aspect of the present application relates to a method for reducing mortality caused by the secondary effect of a pathogenic infection in a subject. The method comprises: administering into a subject in need of such treatment an effective amount of a neuregulin. In one embodiment, the method further comprises administering into the subject a secondary active agent selected from the group consisting of HEME neutralization agent, CXCL10 inhibitor, CXCR3 inhibitor, STAT3 inhibitor, anti-inflammatory agent, antimicrobial agent and combinations thereof. In another embodiment, the pathogen infection is cerebral malaria.

In some embodiments, the neuregulin is administered in a dosage range from about 1 µg/kg body weight/day to about 100 mg/kg body weight/day, about 10 µg/kg body weight/day to about 100 mg/kg body weight/day, about 100 µg/kg body weight/day to about 100 mg/kg body weight/day, or about 1 mg/kg body weight/day to about 100 mg/kg body weight/day.

In another embodiment, the neuregulin is co-administered with at least one secondary active agent.

In certain embodiment, the secondary active agent is a HEME neutralization agent, a CXCL10 inhibitor, a CXCR3 inhibitor, a STAT3 inhibitor, an anti-inflammatory agent, an antimicrobial agent or combination thereof.

HEME Neutralization Agents.

The HEME-HEME oxygenase system possesses important regulatory properties involved in both physiological as well as pathophysiological processes, such as cytoprotection, apoptosis and inflammation. In moderate quantities when bound to protein, HEME forms an essential element for various biological processes, but when present in large quantities, it can become toxic by mediating oxidative stress and inflammation. The effect of free HEME on the vascular system is determined by extracellular factors, such as hemoglobin/HEME-binding proteins, haptoglobin, albumin and hemopexin and intracellular factors, including HEME oxygenases and ferritin. HEME oxygenase (HO) enzyme activity results in the degradation of HEME and the production of iron, carbon monoxide and biliverdin. Each of these HEME-degradation products is potentially toxic, but may also provide strong cytoprotection, depending on the generated amounts and the microenvironment. To date, two active isozymes, HO-1 (HSP-32) and HO-2 have been described. HO-1 and HO-2 are the catalytically active forms and have been well characterized. Pre-induction of HO activity has been demonstrated to ameliorate inflammation and mediate potent resistance to oxidative injury.

A "HEME neutralization agent," as used herein is any agent capable of reducing or disrupting HEME toxicity. The HEME neutralization agent may reduce HEME toxicity by neutralizing or reducing HEME activity or degrading HEME directly or indirectly by activating agents that catalyze HEME degradation, such as HEME oxygenase.

Exemplary HEME neutralization agents include, but are not limited to HEME oxygenase, HEME oxygenase activators, heavy metal salts, such as cadmium chloride and cobalt chloride, clotrimazole, miconazole, ketoconazole, rhein and diacerhein, including derivatives combinations thereof.

Exemplary HEME oxygenase activators include, but are not limited to hemin, bilirubin, carbon monoxide, triterpenoid CDDO compounds, such as 2-cyano-3,12-dioxooleana-1,9(11)-dien-28-oic acid (CDDO), 1-[2-cyano-3,12-dioxooleana-1,9(11)-dien-28-oyl]imidazole (CDD-imidazolide or CDD-Im), methyl-2-cyano-3,12-dioxooleana-1,9-dien-28-oate (CDDO-methyl ester or CDDO-Me) and others described in U.S. Pat. Nos. 6,326,507, 6,552,075 and 7,435,755; nitric oxide, hydrogen peroxide, quinones, including menadione, probucol, probucol dithiobisphenol (DTBP), cytokines, such as interleukin-10 and interleukin-13, cobalt protoporphyrin (CoPP), oxidized LDL, linoleyl hydroperoxide, rapamycin, statins, probucol, aspirin and dopamine, including derivatives combinations thereof.

CXCL10/CXCR3 Inhibitors.

CXCL10 is a cytokine belonging to the CXC chemokine family. CXCL10 is a chemokine ligand for the CXCR3 chemokine receptor, a member of the chemokine receptor family of G protein coupled receptors (GPCRs). In addition, CXCL10 and CXCR3 are locally upregulated and are known to be activated in inflammation various inflammatory diseases. Therefore, in some embodiments, the secondary active agent may be an antagonist or inhibitor of CXCL10 or CXCR3. CXCL10 is expressed early in mice infected with *P. berghei* ANKA (ECM) as well as in human CM. The terms "CXCL10 inhibitor" and "CXCR3 inhibitor," as used herein, refer to any agent capable of reducing or disrupting CXCL10 and CXCR3 signalling in a cell, respectively. The term "CXCL10/CXCR3 inhibitors" refer to inhibitors to CXCL10 or CXCR3 or both. Exemplary CXCL10/CXCR3 inhibitors, include but are not limited to anti-CXCL10 antibodies, anti-CXCR3 antibodies, inhibitory polynucleotides or oligonucleotides that reduce CXCL10 or CXCR3 transcription or translation (e.g., antisense, siRNA and shRNA targeting CXCL10 or CXCR3; albuterol, fenoterol, β-funaltrexamine fentanyl, N-terminal truncation mutants of CXCL10 etc.

STAT3 Inhibitors.

The signal transducer and activator of transcription (STAT3) is a signaling molecule which can be activated by pro- and ant-inflammatory stimuli and cellular stresses, therefore STAT3 can be either pro-inflammatory and anti-inflammatory. A "STAT3 inhibitor," as used herein, is any agent capable of reducing or disrupting STAT3 signaling in a cell. Exemplary STAT3 inhibitors include, but are not limited to anti-STAT3 antibodies; inhibitory polynucleotides or oligonucleotides that reduce STAT3 transcription or translation (e.g., antisense, siRNA, shRNA targeting STAT3); tyrphostin AG490; flavopiridol; a platinum (IV) compound, such as CPA-1, CPA-3 CPA-7, platinum (IV) tetrachloride or IS3 295 (obtainable from the NCl diversity set, NSC 295558); a quinolinecarboxamide derivative as described in U.S. Patent Application No. 20110172429; cucurbitacin I, curcumin, magnolol, indirubin, resveratol, flavopriridol, galiellalacton, JSI-124, piceatannol, NSC 74859, 531-M2001, AP23573, AP23841, CCI-779 and RAD001.

Anti-Inflammatory Agents.

In certain embodiments, the secondary active agent is an anti-inflammatory agent, such as a small molecule chemical compound or one of the other anti-inflammatory agents described herein. As used herein, the term "anti-inflammatory agent" refers to an agent causing a reduction or prevention of inflammation in a tissue. A reduction in inflammation may include, for example, reducing the secretion or expression of inflammatory cytokines, chemokines, cytokine/chemokine receptors, adhesion molecules, proteases and/or immunoglobulins; reducing chemotaxis or migration of cells; reducing the blood concentration of monocytes and/or local accumulation thereof at the sites of inflammation; increasing apoptosis of immune cells; suppressing class-II MHC presentation; reducing the number of autoreactive cells; increasing immune tolerance, reducing autoreactive cell survival, combinations thereof and the like.

Exemplary small molecule compounds that can be used as secondary anti-inflammatory agent include, but are not are not limited to, small molecule compounds or medicaments selected from the group consisting of analgesics, such as aspirin or TYLENOL® (Acetaminophen); 2-amino-6-aryl-5-substituted pyrimidines; nonsteroidal anti-inflammatory drugs (NSAIDs), such as acemetacin, amtolmetin, azapropazone, benorilate, benoxaprofen, benzydamine hydrochloride, bromfenal, bufexamac, butibufen, carprofen, celecoxib, choline salicylate, diclofenac dipyone, droxicam, etodolac, etofenamate, etoricoxib, felbinac, fentiazac, floctafenine, ibuprofen, indoprofen, isoxicam, lomoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, trolamine salicylate, zomepirac, aclofenac, aloxiprin, naproxen, aproxen, aspirin, diflunisal, fenoprofen, indomethacin, mefenamic acid, piroxicam, phenylbutazone, salicylamide, salicylic acid, sulindac, desoxysulindac, tenoxicam, tramadol, ketorolac, clonixin, fenbufen, benzydamine hydrochloride, meclofenamic acid, flufenamic acid or tolmetin; ganciclovir; glucocorticoids such as cortisol or aldosterone; cyclooxygenase inhibitors; 5-lipoxygenase inhibitors; leukotriene receptor agents; purine agents, such as azathioprine and mycophenolate mofetil (MMF); alkylating agents, such as cyclophosphamide; bromocriptine; danazol; dapsone; glutaraldehyde; cyclosporine; 6 mercaptopurine; corticosteroids, including oral glucocorticosteroids or glucocorticoid analogs, e.g., prednisone; methylprednisolone, including SOLU-MEDROL® and methylprednisolone sodium succinate, triamcinolone and betamethasone, dexamethasone; aminosalicylate; azathioprine, calcineurin inhibitors, such as cyclosporine, tacrolimus (FK-506) and sirolimus (rapamycin); RS-61443 (mycophenolate mofetil); dihydrofolate reductase inhibitors, such as methotrexate (oral or subcutaneous); mitoxantrone (NOVANTRONE®; Immunex Corporation), interferon β-1a (AVONEX®; Ares-Sorono Group), interferonβ-1b (BETASERON®; Berlex Laboratories, Inc.); and glatiramer acetate (COPAXONE; Teva Pharmaceuticals).

In certain embodiments, the anti-inflammatory agent binds specifically to a cytokine, chemokine and/or its corresponding receptor. Exemplary cytokine or cytokine receptor targets and/or their reactive inhibitory products include, but are not limited to, interferon-α, -β or -γ; tumor necrosis factor (TNF)-alpha, e.g., (infliximab (REMICADE®), adalimumab (HUMIRA®), D2E7 (BASF Pharma) and HUMICADE® (Celltech)); soluble forms of the TNF receptor (etanercept (ENBREL®)); CD20, including rituximab (RITUXAN®), humanized 2H7, 2F2 (Hu-Max-CD20), human CD20 antibody (Genmab) and humanized A20 antibody (Immunomedics); TNF-beta; interleukin-2 (IL-2), including daclizumab; IL-2 receptor, interleukin-4 (IL-4) and IL-4 receptor; interleukin-6 (IL-6) and IL-6 receptor; interleukin-1 (IL-1) receptor, including IL-1 receptor agents, such as anakinra (KINERET); LFA-1, including anti-CD 11a, anti-CD 18 antibodies and soluble peptides containing a LFA-3 binding domain; anti-L3T4 antibodies; interleukin-1β (IL-1β); interleukin-8 (IL-8); interferon-γ (IFN-γ); vascular endothelial growth factor (VEGF); leukemia inhibitory factor (LIF); monocyte chemoattractant protein-1 (MCP-1); RANTES; interleukin-10 (IL-10); interleukin-12 (IL-12); matrix metalloproteinase 2 (MMP2); IP-10; macrophage inflammatory protein 1α (MIP 1α); macrophage inflammatory protein 1β (MIP1β); pan-T, including anti-CD3 or anti-CD4/CD4a antibodies; BAFF (zTNF4, BLyS) and BAFF receptor, BR3; anti-idiotypic antibodies for MHC antigens and MHC fragments; CD40 receptor and anti-CD40 ligand (CD154); CTLA4-Ig; T-cell receptor antibodies, such as T10B9; heterologous anti-lymphocyte globulin; streptokinase; transforming growth factor-beta (TGF-beta); streptodomase; RNA or DNA from the host; chlorambucil; deoxyspergualin; T-cell receptor; and T-cell receptor fragments.

Antimicrobial Agents.

In certain embodiments, the secondary active agent is an antimicrobial agent. Exemplary antimicrobial agents include, but are not limited to penicillin, cloxacillin, dicloxacillin, cephalosporin, erythromycin, amoxicillin-clavulanate, ampicillin, tetracycline, trimethoprim-sulfamethoxazole, chloramphenicol, ciprofloxacin, aminoglycoside (e.g., tobramycin and gentamicin), streptomycin, sulfa drugs, kanamycin, neomycin, metronidazole, land monobactams; anti-viral agents, such as amantadine hydrochloride, rimantadin, acyclovir, famciclovir, foscarnet, ganciclovir sodium, idoxuridine, ribavirin, sorivudine, trifluridine, valacyclovir, vangancyclovir, pencyclovir, vidarabin, didanosine, stavudine, zalcitabine, zidovudine, interferon alpha and edoxudine; antifungal agents such as terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin and selenium sulfide, including derivatives combinations thereof.

In certain preferred embodiments, a neuregulin is administered in combination with an antimalarial agent. Exemplary antimalarial agents include artemisinin, artemisinn derivatives, such as artemether and artesunate, dihydroartemisinin, artemotel, artemether/lumefantrine, chloroquine, hydroxychloroquine (PLAQUENIL), quinine, quinimax, mefloquine, primaquine, quinidine, amodiaquine, atavaquone, halofantrine, doxycycline, clindamycin, sulfasalazine (AZULFIDINE), sulfadoxine, sulfamethoxypyridazinem proguanil, pyrimethamine and leflunomide, including derivatives combinations thereof.

In some embodiments, the secondary active agent comprises an antibody, short interfering RNA (siRNA), aptamer, synbody, target neutralization agent, peptide, aptamer-siRNA chimera, single stranded antisense oligonucleotide, triplex forming oligonucleotide, ribozyme, external guide sequence or antagonist encoded expression vector.

Antibodies as Secondary Active Agents.

In some embodiments, a secondary active agent may comprise an antibody antagonist against CXCL10, CXCR3 or HEME. In one embodiment, the antibody antagonist is an anti-CXCL10 antibody. In another embodiment, the antibody antagonist is one which binds to human CXCR3 and preferably blocks (partially or completely) the ability of a cell carrying the receptor, such as an epithelial, endothelial or lymphoid cell, from binding to and/or being activated by chemokine ligand, such as CXCL10. In yet another embodiment, the antibody antagonist is an anti-HEME antibody.

In one embodiment, the antibody antagonist is a monoclonal antibody. In another embodiment, the antibody antagonist is a humanized antibody. In another embodiment, the antibody antagonist is an antibody fragment. In yet another embodiment, the antibody antagonist is a humanized antibody fragment.

The antibody antagonist may be administered in any form suitable for neutralizing CXCL10 and/or CXCR3 activity. Exemplary antibody or antibody derived fragments may include any member of the group consisting of: IgG, antibody variable region; isolated CDR region; single chain Fv molecule (scFv) comprising a VH and VL domain linked by a peptide linker allowing for association between the two domains to form an antigen binding site; bispecific scFv dimer; minibody comprising a scFv joined to a CH3 domain; diabody (dAb) fragment; single chain dAb fragment consisting of a VH or a VL domain; Fab fragment consisting of VL, VH, CL and CH1 domains; Fab' fragment, which differs from a Fab fragment by the addition of a few residues at the carboxyl terminus of the heavy chain CH1 domain, including one or more cysteines from the antibody hinge region; Fab'-SH fragment, a Fab' fragment in which the cysteine residue(s) of the constant domains bear a free thiol group; F(ab')2, bivalent fragment comprising two linked Fab fragments; Fd fragment consisting of VH and CH1 domains; derivatives thereof; and any other antibody fragment(s) retaining antigen-binding function. Fv, scFv or diabody molecules may be stabilized by the incorporation of disulphide bridges linking the VH and VL domains. When using antibody-derived fragments, any or all of the targeting domains therein and/or Fc regions may be "humanized" using methodologies well known to those of skill in the art. In some embodiments, the anti-inflammatory antibody is modified to remove the Fc region.

In certain embodiments, the anti-CXCR3 antibody or antibody fragment thereof is conjugated to or fused to a second antibody or antibody binding fragment to enhance its binding to target cells carrying the CXCR3 receptor.

Short Interfering RNAs (siRNAs).

An siRNA is a double-stranded RNA that can be engineered to induce sequence-specific post-transcriptional gene silencing of mRNAs corresponding to CXCL10, CXCR3 or HEME. siRNAs exploit the mechanism of RNA interference (RNAi) for the purpose of "silencing" gene expression of e.g., targeted chemokine-, cytokine- or receptor genes. This "silencing" was originally observed in the context of transfecting double stranded RNA (dsRNA) into cells. Upon entry therein, the dsRNA was found to be cleaved by an RNase III-like enzyme, Dicer, into double stranded small interfering RNAs (siRNAs) 21-23 nucleotides in length containing 2 nucleotide overhangs on their 3' ends. In an ATP dependent step, the siRNAs become integrated into a multi-subunit RNAi induced silencing complex (RISC) which presents a signal for AGO2-mediated cleavage of the complementary mRNA sequence, which then leads to its subsequent degradation by cellular exonucleases.

In one embodiment, the secondary active agent comprises a synthetic siRNA targeting CXCL10, CXCR3, HEME or combination thereof. Synthetically produced siRNAs structurally mimic the types of siRNAs normally processed in cells by the enzyme Dicer. Synthetically produced siRNAs may incorporate any chemical modifications to the RNA structure that are known to enhance siRNA stability and functionality. For example, in some cases, the siRNAs may be synthesized as a locked nucleic acid (LNA)-modified siRNA. An LNA is a nucleotide analogue that contains a methylene bridge connecting the 2'-oxygen of the ribose with the 4' carbon. The bicyclic structure locks the furanose ring of the LNA molecule in a 3'-endo conformation, thereby structurally mimicking the standard RNA monomers.

In other embodiments, the anti-inflammatory agent may comprise an expression vector engineered to transcribe a short double-stranded hairpin-like RNA (shRNA) that is processed into a targeted siRNA inside the cell. The shRNAs can be cloned in suitable expression vectors using kits, such as Ambion's SILENCER® siRNA Construction Kit, Imgenex's GENESUPPRESSOR™ Construction Kits and Invitrogen's BLOCK-IT™ inducible RNAi plasmid and lentivirus vectors.

Synthetic siRNAs and shRNAs may be designed using well known algorithms and synthesized using a conventional DNA/RNA synthesizer. A variety of chemokine-, cytokine- and receptor-targeted siRNAs may be commercially obtained from Origen (Rockville, Md.).

Target Neutralization Agents.

In some embodiments, the secondary active agent is a target neutralization agent. As used herein, the term "target neutralization agent" refers to any non-antibody protein, peptide or synthetic binding molecule, such as an aptamer or synbody, which is capable of specifically binding directly or indirectly to CXCL10, CXCR3 or HEME so as to inhibit a biological activity associated with reducing or preventing an inflammatory response and/or tissue damage.

The target neutralization agents may be produced by any conventional method for generating high-affinity binding ligands, including SELEX, phage display and other methodologies, including combinatorial chemistry- and/or high throughput methods known to those of skill in the art.

An aptamer is a nucleic acid version of an antibody that comprises a class of oligonucleotides that can form specific three dimensional structures exhibiting high affinity binding to a wide variety of cell surface molecules, proteins and/or macromolecular structures. Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Typically, aptamers are small nucleic acids ranging from 15-50 bases in length that fold into defined secondary and tertiary structures, such as stem-loops or G-quartets.

An aptamer can be chemically linked or conjugated to the above described nucleic acid inhibitors to form targeted nucleic acid inhibitors, such as aptamer-siRNA chimeras. An aptamer-siRNA chimera contains a targeting moiety in the form of an aptamer which is linked to an siRNA. When using an aptamer-siRNA chimera, it is preferable to use a cell internalizing aptamer. Upon binding to specific cell surface molecules, the aptamer can facilitate internalization into the cell where the nucleic acid inhibitor acts. In one embodiment both the aptamer and the siRNA comprises RNA. The aptamer and the siRNA may comprise any nucleotide modifications as further described herein. Preferably, the aptamer comprises a targeting moiety specifically directed to binding cells expressing the chemokine-, cytokine- and/or receptor target genes, such as lymphoid, epithelial cell and/or endothelial cells.

Synbodies are synthetic antibodies produced from libraries comprised of strings of random peptides screened for binding to target proteins of interest.

Target neutralization agent agents, including aptamers and synbodies, can be engineered to bind target molecules very tightly with Kds between $10^{-10}$ to $10^{-12}$ M. In some embodiments, the target neutralization agent binds the target molecule with a Kd less than $10^{-6}$, less than $10^{-8}$, less than $10^{-9}$, less than $10^{-10}$ or less than $10^{-12}$ M.

Antisense Oligonucleotides.

In some embodiments, the secondary active agent comprises an antisense oligonucleotide or polynucleotide capable of inhibiting the expression of CXCL10, CXCR3 or HEME. The antisense oligonucleotide or polynucleotide may comprise a DNA backbone, RNA backbone or chemical derivative thereof. In one embodiment, the antisense oligonucleotide or polynucleotide comprises a single stranded antisense oligonucleotide or polynucleotide targeting for degradation. In certain embodiments, the anti-inflammatory agent comprises a single stranded antisense oligonucleotide complementary to a CXCL10, CXCR3 or HEME mRNA sequence. The single stranded antisense oligonucleotide or polynucleotide may be synthetically produced or it may be expressed from a suitable expression vector. The antisense nucleic acid is designed to bind via complementary binding to the mRNA sense strand so as to promote RNase H activity, which leads to degradation of the mRNA. Preferably, the antisense oligonucleotide is chemically or structurally modified to promote nuclease stability and/or increased binding.

In some embodiments, the antisense oligonucleotides are modified to produce oligonucleotides with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.) or alkylators and/or modified linkages (e.g., alpha anomeric nucleic acids, etc.).

In some embodiments, the single stranded oligonucleotides are internally modified to include at least one neutral charge in its backbone. For example, the oligonucleotide may include a methylphosphonate backbone or peptide nucleic acid (PNA) complementary to the target-specific sequence. These modifications have been found to prevent or reduce helicase-mediated unwinding. The use of uncharged probes may further increase the rate of hybridization to polynucleotide targets in a sample by alleviating the repulsion of negatively-charges nucleic acid strands in classical hybridization.

PNA oligonucleotides are uncharged nucleic acid analogs for which the phosphodiester backbone has been replaced by a polyamide, which makes PNAs a polymer of 2-aminoethylglycine units bound together by an amide linkage. PNAs are synthesized using the same Boc or Fmoc chemistry as are use in standard peptide synthesis. Bases (adenine, guanine, cytosine and thymine) are linked to the backbone by a methylene carboxyl linkage. Thus, PNAs are acyclic, achiral and neutral. Other properties of PNAs are increased specificity and melting temperature as compared to nucleic acids, capacity to form triple helices, stability at acid pH, non-recognition by cellular enzymes like nucleases, polymerases, etc.

Methylphosphonate-containing oligonucleotides are neutral DNA analogs containing a methyl group in place of one of the non-bonding phosphoryl oxygens. Oligonucleotides with methylphosphonate linkages were among the first reported to inhibit protein synthesis via anti-sense blockade of translation.

In some embodiments, the phosphate backbone in the oligonucleotides may contain phosphorothioate linkages or phosphoroamidates. Combinations of such oligonucleotide linkages are also within the scope of the present invention.

In other embodiments, the oligonucleotide may contain a backbone of modified sugars joined by phosphodiester internucleotide linkages. The modified sugars may include furanose analogs, including but not limited to 2-deoxyribofuranosides, α-D-arabinofuranosides, α-2'-deoxyribofuranosides and 2',3'-dideoxy-3'-aminoribofuranosides. In alternative embodiments, the 2-deoxy-β-D-ribofuranose groups may be replaced with other sugars, for example, β-D-ribofuranose. In addition, β-D-ribofuranose may be present wherein the 2-OH of the ribose moiety is alkylated with a C1-6 alkyl group (2-(O—C1-6 alkyl)ribose) or with a C2-6 alkenyl group (2-(O—C2-6 alkenyl)ribose) or is replaced by a fluoro group (2-fluororibose).

Related oligomer-forming sugars include those used in locked nucleic acids (LNA) as described above. Exemplary LNA oligonucleotides include modified bicyclic monomeric units with a 2'-O-4'-C methylene bridge, such as those described in U.S. Pat. No. 6,268,490.

Chemically modified oligonucleotides may also include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-[2-(1H-indole-3yl)ethyl]carboxyamide)-2'-deoxyuridine, 5-(N-[1-(3-trimethylammonium)propyl]carboxyamide)-2'-deoxyuridine chloride, 5-(N-napthylcarboxyamide)-2'-deoxyuridine, 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, methylations, unusual base-pairing combinations, such as the isobases isocytidine and isoguanidine and the like.

Ribozymes.

In some embodiments, the secondary active agent comprises a ribozyme capable of inhibiting the expression of CXCL10, CXCR3 or HEME. Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes and tetrahymena ribozymes. There are also a number of ribozymes that are not found in natural systems, but which have been engineered to catalyze specific reactions de novo. Preferred ribozymes cleave RNA or DNA substrates and more preferably cleave RNA substrates, such as CXCL10 or CXCR3 mRNAs. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex Forming Oligonucleotides (TFOs).

In some embodiments, the secondary active agent comprise triplex forming oligonucleotide capable of inhibiting the expression of CXCL10, CXCR3 or HEME. Triplex forming oligonucleotides (TFOs) are molecules that can interact with either double-stranded and/or single-stranded nucleic acids, including both coding and non-coding regions in genomic DNA targets. When TFOs interact with a target region, a structure called a triplex is formed, in which there are three strands of DNA forming a complex dependant on both Watson-Crick and Hoogsteen base-pairing. TFOs can bind target regions with high affinity and specificity. In preferred embodiments, the triplex forming molecules bind the target molecule with a Kd less than 10-6, 10-8, 10-10 or 10-12. Exemplary TFOs for use in the present invention include PNAs, LNAs and LNA modified PNAs, such as Zorro-LNAs.

External Guide Sequences (EGSs).

External guide sequences (EGSs) are molecules that bind a target nucleic acid molecule forming a complex and this complex is recognized by RNase P, which cleaves the target molecule. EGSs can be designed to specifically target an mRNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In certain embodiments, the tissue damage is accompanied by occlusion of vessels, glial activation, focal inflammation, activation of apoptosis, reversible neuronal tissue damage and/or irreversible neuronal tissue damage.

In other embodiments, the subject is diagnosed with an inflammatory disorder or pathogenic infection that results in elevated expression or activity of CXCL10, STAT3 and/or HEME.

In one embodiment, the inflammatory disorder or pathogenic infection is an inflammatory disease of the central or peripheral nervous system selected from the group consisting of abscess, AIDS related infections, Alzheimer's disease, chronic fatigue syndrome, congenital infections, encephalitis, ischemia/stroke, meningitis, migraine, multiple sclerosis and traumatic brain injury.

In another embodiment, the inflammatory disorder or pathogenic infection is an inflammatory disease of the urogenital system selected from the group consisting of endometriosis, glomerulosclerosis, infections of the vagina and cervix, intra-amniotic infection, pelvic inflammatory disease, renal inflammation/nephritis, sexually transmitted diseases, urethritis, urinary tract infections and yeast infections.

In another embodiment, the inflammatory disorder or pathogenic infection is an inflammatory disease of the digestive system selected from the group consisting of colon cancer, hepatitis, inflammatory bowel disease, interstitial cystitis, irritable bowel syndrome and ulcers.

In another embodiment, the inflammatory disorder or pathogenic infection is an inflammatory disease of the respiratory system selected from the group consisting of chronic lung disease, asthma, tuberculosis and pneumonia.

In another embodiment, the inflammatory disorder or pathogenic infection is an inflammatory disease of the skin, integument and/or musculoskeletal system selected from the group consisting of Behcet's Disease, Crohn's disease, dermatitis, gingivitis, gout, myalgia, osteoarthritis, periodontitis, psoriasis, rheumatoid arthritis, spondyloarthropathies and skin sunburn.

In another embodiment, the inflammatory disorder or pathogenic infection is an inflammatory disease of the cardiovascular system selected from the group consisting of atherosclerosis, pericarditis, endocarditis, Kawasaki's Disease, myocarditis, rheumatic fever and vasculitis.

In another embodiment, the inflammatory disorder or pathogenic infection is selected from the group consisting of autoimmune diseases, cat scratch disease, eye infections, Lyme disease, lymphadenopathy, lymphatic inflammation, opportunistic infections, radiation-induced inflammation, sarcoidosis, Sjogren's syndrome and systemic lupus erythematosus (SLE or lupus) and related disorders.

In another embodiment, the inflammatory disorder or pathogenic infection is caused by an infectious agent or corresponding disease selected from the group consisting of bacterial infections, sepsis, fungal infections, parasitic infections, cerebral malaria, prion protein infections, toxic compounds, nerve agents and viral infections.

The pathogenic infection caused may be caused by bacteria, fungi and/or protozoans. Exemplary bacteria include, but are not limited to, *Staphylococcus* species, including *S. epidermidis, S. aureus* and methicillin-resistant *S. aureus; Enterococcus* species, including *E. faecalis* and *E. faecium; Mycobacterium tuberculosis, Haemophilus influenzae, Pseudomonas* species, including *P. aeruginosa, P. pseudomallei* and *P. mallei; Salmonella* species, including *S. enterocolitis, S. typhimurium, S. enteritidis, S. bongori* and *S. choleraesuis; Shigella* species, including *S. flexneri, S. sonnei, S. dysenteriae* and *S. boydii; Brucella* species, including *B. melitensis, B. suis, B. abortus* and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Chlamydia trachomatis, Clostridium difficile, Cryptococcus neoformans, Moraxella catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis; Listeria monocytogenes, Nocardia asteroides, Bacteroides* species, Actinomycetes species, *Treponema pallidum, Leptospirosa* species, *Klebsiella pneumoniae; Proteus* sp., including *Proteus vulgaris; Serratia* species, *Acinetobacter, Yersinia* species, including *Y. pestis* and *Y. pseudotuberculosis; Francisella tularensis, Enterobacter* species, *Bacteriodes* species, *Legionella* species, *Borrelia burgdorferi* and the like.

Exemplary fungi include, but are not limited to, *Aspergillus* species, *Dermatophytes, Blastomyces derinatitidis, Candida* species, including *C. albicans* and *C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. erinacei* and *T. verrucosum; Microsporum* species, including *M. audouini, M. ferrugineum, M. canis, M. nanum, M. distortum, M. gypseum, M. fulvum* and the like.

Exemplary protozoans include, but are not limited to *Cryptosporidium, Isospora belli, Toxoplasma gondii, Trichomonas vaginalis* and *Cyclospora* species.

Administration of Neuregulin and/or Secondary Active Agents.

The neuregulins and/or other secondary active agents of the present invention may be administered to the subject with known methods, such as intravenous administration as a bolus or by continuous infusion over a period of time, by intramuscular, intraperitoneal, intracerobrospinal, subcutaneous, intra-articular, intrasynovial, intrathecal oral, topical or inhalation routes.

In some embodiments, the neuregulin or secondary active agent is administered in a dosage range from 0.1 µg/kg body weight/day to about 100 mg/kg body weight/day, 1 µg/kg body weight/day to about 100 mg/kg body weight/day, about 10 µg/kg body weight/day to about 100 mg/kg body weight/day, about 100 µg/kg body weight/day to about 100 mg/kg body weight/day, about 1 mg/kg body weight/day to about 100 mg/kg body weight/day, or about 5 mg/kg body weight/day to about 50 mg/kg body weight/day.

In certain embodiments, the active agent(s) may be administered directly to a tissue, such as a damaged and/or inflammed tissue. For example, in the case of inflammatory bowel disorders, mucosal tissue may be directly contacted with the active agent(s). For skin inflammatory diseases such as psoriasis, dermal tissue may be contacted directly with the active agent(s) in a cream, lotion or ointment. For asthma, pulmonary tissue, e.g., bronchoalveolar tissue may be contacted by inhalation of a liquid or powder aspirate. The active agent may also be placed on a solid support such as a sponge or gauze for administration against the target chemokine to the affected tissues.

The active agents of the instant application can be administered in the usually accepted pharmaceutically acceptable carriers. Acceptable carriers include, but are not limited to, saline, buffered saline and glucose in saline. Solid supports, liposomes, nanoparticles, microparticles, nanospheres or microspheres may also be used as carriers for administration of the active agents.

The appropriate dosage ("therapeutically effective amount") of the active agents will depend, for example, on the condition to be treated, the severity and course of the condition, the mode of administration, whether the antibody or agent is administered for preventive or therapeutic purposes, the bioavailability of the particular agent(s), previous therapy, the age and weight of the patient, the patient's clinical history and response to the antibody, the type of the active agent used, discretion of the attending physician, etc. The active agent is suitably administered to the patent at one time or over a series of treatments and may be administered to the patient at any time from diagnosis onwards. The active agent may be administered as the sole treatment or in conjunction with other drugs or therapies useful in treating the condition in question.

As a general proposition, the therapeutically effective amount of the active agent is administered will be in the range of about 0.1 µg/kg body weight/day to about 1000 mg/kg body weight/day whether by one or more administrations. In a particular embodiments, the range of the active agent administered is from about 1 µg/kg body weight/day to about 1000 mg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 1000 mg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 mg/kg body weight/day to about 100 µg/kg body weight/day, about 100 µg/kg body weight/day to about 1000 mg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 1000 mg/kg body weight/day, about 1 mg/kg body weight/day to about 100 mg/kg body weight/day, about 1 mg/kg body weight/day to about 10 mg/kg body weight/day, about 10 mg/kg body weight/day to about 1000 mg/kg body weight/day, about 10 mg/kg body weight/day to about 100 mg/kg body weight/day, about 100 mg/kg body weight/day to about 1000 mg/kg body weight/day, about 0.05 mg/kg body weight/day to about 50 mg/kg body weight/day, about 0.5 mg/kg body weight/day to about 50 mg/kg body weight/day or about 5 mg/kg body weight/day to about 50 mg/kg body weight/day.

In another embodiment, the active agent is administered at a daily dosage range of about 0.1 µg to about 5 g, about 0.1 µg to about 1 g, about 0.1 µg to about 100 mg, about 0.1 µg to about 10 mg, about 0.1 µg to about 1 mg, about 0.1 µg to about 100 µg, about 0.1 µg to about 10 µg, about 0.1 µg to about 1 µg, about 1 µg to about 5 g, about 1 µg to about 1 g, about 1 µg to about 100 mg, about 1 µg to about 10 mg, about 1 µg to about 1 mg, about 1 µg to about 100 µg, about 1 µg to about 10 µg, about 10 µg to about 5 g, about 10 µg to about 1 g, about 10 µg to about 100 mg, about 10 µg to about 10 mg, about 10 µg to about 1 mg, about 10 µg to about 100 µg, about 100 µg to about 5 g, about 100 µg to about 1 g, about 100 µg to about 100 mg, about 100 µg to about 10 mg, about 100 µg to about 1 mg, about 1 mg to about 5 g, about 1 mg to about 1 g, about 1 mg to about 100 mg, about 1 mg to about 10 mg, about 100 mg to about 5 g and about 100 mg to about 1 g. As expected, the dosage will be dependant on the condition, size, age and condition of the patient.

The neuregulin and/or a secondary active agent(s) may be administered at various times following the onset or diagnosis of the inflammatory disorder or pathogenic. Thus, the neuregulin and/or a secondary active agent(s) may be administered within 3 hours, within 6 hours, within 12 hours, within 24 hours, within 48 hours, within 72 hours, within 4 days, within 5 days, within 6 days, within 7 days or within 10 days of the onset of the inflammatory disorder or pathogenic infection.

The active agent(s) may be administered, as appropriate or indicated, a single dose as a bolus or by continuous infusion or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks, monthly or in combination(s) thereof. The progress of the therapy can be easily monitored by conventional techniques.

Compositions and Kits for Treating Inflammatory Disorders and Pathogenic Infections Another aspect of the present invention relates to a pharmaceutical composition for treating inflammatory disorders and pathogenic infections comprising a neuregulin, a pharmaceutically acceptable carrier and optionally, at least one secondary active agent is a HEME neutralization agent, a CXCL10 inhibitor, a CXCR3 inhibitor, a STAT3 inhibitor, an anti-inflammatory agent, an antimicrobial agent or combination thereof.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous oral, transdermal (topical) and transmucosal administration. Solutions or suspensions used for parenteral, intradermal or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol and the like) and suitable mixtures thereof. The proper fluidity can be maintained, for example, by the use of a coating such as lecithin, by the maintenance of the requited particle size in the case of dispersion and by the use of surfactants. In many cases, it will be preferable to include isotonic agents, for example, sugars, polyalcohols such as manitol, sorbitol and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid carrier for use as a mouthwash, wherein the compound in the fluid carrier is applied orally and swished and expectorated or swallowed. Pharmaceutically compatible binding agents and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Stertes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from pressured container or dispenser which contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art and include, for example, for transmucosal administration, detergents, bile salts and fusidic acid derivatives. Transmucosal administration can be accomplished through the use of nasal sprays or suppositories. For transdermal administration, the pharmaceutical compositions are formulated into ointments, salves, gels or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from e.g., Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. In certain embodiments, single dosage contains 1 μg to 500 mg, 0.1 mg to 100 mg, or 1 mg to 50 mg of a neuregulin.

In another aspect, the present invention also encompasses kits for preventing or ameliorating tissue damage caused by the above-described inflammatory disorders and pathogenic infections. The kits comprise one or more effective doses of one or more active agents, including at least one neuregulin. In certain embodiments, the kits can comprise components useful for carrying out the methods such as devices for delivering the neuregulin. In certain other embodiments, the kits can further contain a secondary active agent to be administered in conjunction with the neuregulin.

Methods of Producing Neuregulins

The neuregulins or variants thereof may be produced using methods well known in the art. In certain embodiments, the neuregulins or variants thereof are produced by chemical synthesis. Briefly, a neuregulin may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the neuregulins may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is PEGylated. This last amino acid is often referred to as a carboxyl-PEG-amine, carboxyl-PEO-amine or amine-PEG-acid, whereby the amine is blocked to protect against reaction and the acid is free to react with the amine group from the previously added amino acid in the reaction. PEG (polyethylene glycol) and PEO (polyethylene oxide) are polymers composed of repeating subunits of ethylene glycol and ethylene oxide monomers. In one embodiment, a PEGylated GGF2/NRG2 (SEQ ID NO:28) would have the PEG moiety connected to the histidine residue (H) at the amino-terminus of the polypeptide. In one embodiment, the PEG moiety is 5 to 30 kDa in size. In another embodiment, the PEG moiety is 10 to 20 kDa in size.

In addition to using PEGylated end amino acid during synthesis, a neuregulin may be PEGylated by PEGylation. PEGylation is the process of covalent attachment of polyethylene glycol polymer chains to another molecule, normally a drug or therapeutic protein. PEGylation can be achieved by incubation of a reactive derivative of PEG with the target neuregulin. The covalent attachment of PEG to a neuregulin can "mask" the neuregulin from the host's immune system (reduced immunogenicity and antigenicity), increase the hydrodynamic size (size in solution) of the neuregulin which prolongs its circulatory time by reducing renal clearance. PEGylation can also provide water solubility to hydrophobic proteins.

The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional."

The chemically active or activated derivatives of the PEG polymer are prepared to attach the PEG to the desired molecule.

The overall PEGylation processes used to date for protein conjugation can be broadly classified into two types, namely a solution phase batch process and an on-column fed-batch process. The simple and commonly adopted batch process involves the mixing of reagents together in a suitable buffer solution, preferably at a temperature between 4 and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, are made available for protein conjugation.

In certain embodiments, heterobifunctional PEGs are used for conjugation. These heterobifunctional PEGs are very useful in linking two entities, where a hydrophilic, flexible and biocompatible spacer is needed. Preferred end groups for heterobifunctional PEGs are male imide, vinyl sulfones, pyridyl disulfide, amine, carboxylic acids and NHS esters.

In other embodiments, the pegylation agents contain branched, Y shaped or comb shaped polymers that show reduced viscosity and lack of organ accumulation.

In other embodiments, neuregulins or variants thereof are produced using recombinant DNA technologies. Procedures for the expression and purification of recombinant proteins are well established.

In order to express a neuregulin in a biological system, a polynucleotide that encodes the neuregulin is constructed. In certain embodiments, the recombinant polynucleotide is codon optimized for expression in a selected prokaryotic or eukaryotic host cell, such as a mammalian, plant or insect cell. To facilitate replication and expression, the polynucleotide can be incorporated into a vector, such as a prokaryotic or a eukaryotic expression vector. Although the polynucleotide disclosed herein can be included in any one of a variety of vectors (including, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the polynucleotide encoding the neuregulin chimera is typically arranged in proximity and orientation to an appropriate transcription control sequence or promoter to direct mRNA synthesis. That is, the polynucleotide sequence of interest is operably linked to an appropriate transcription control sequence.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers and silencers) which regulate activation or repression of genes operably linked thereto in response to developmental and/or external stimuli and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

Examples of such promoters include: the immediate early promoter of CMV, LTR or SV40 promoter, polyhedron promoter of baculovirus, E. coli lac or trp promoter, phage T7 and lambda $P_L$ promoter and other promoters known to control expression of genes in prokaryotic or eukaryotic cells or their viruses. The expression vector typically also contains a ribosome binding site for translation initiation and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture or such as tetracycline or ampicillin resistance in E. coli.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide coding sequence or a portion thereof, is inserted, exogenous translational control signals, including an ATG initiation codon is provided for expression of the neuregulin sequence. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. (1994) Results Probl Cell Differ 20:125-62; Bitter et al. (1987) Methods in Enzymol 153:516-544).

Expression vectors carrying the neuregulins can be introduced into host cells by any of a variety of well-known procedures, such as electroporation, liposome mediated transfection, calcium phosphate precipitation, infection, transfection and the like, depending on the selection of vectors and host cells.

Host cells that contain neuregulin-encoding nucleic acids are, thus, also a feature of this disclosure. Favorable host cells include prokaryotic (i.e., bacterial) host cells, such as E. coli, as well as numerous eukaryotic host cells, including fungal (e.g., yeast, such as Saccharomyces cerevisiae and Picchia pastoris) cells, insect cells, plant cells and mammalian cells (such as CHO cells). Recombinant neuregulin nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as E. coli, Streptomyces and Salmonella typhimurium; fungal cells, such as Saccharomyces cerevisiae, Pichia pastoris and Neurospora crassa; insect cells such as Drosophila and Spodoptera frugiperda; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants or amplifying the inserted polynucleotide sequences. The culture conditions, such as temperature, pH and the like, are typically those previously used with the host cell selected for expression and will be apparent to those skilled in the art.

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but are not limited to, multifunctional E. coli cloning and expression vectors such as BLUESCRIPT (Stratagene), in which the coding sequence of interest, e.g., a polynucleotide of the invention as described above, can be ligated into the vector in-frame with e.g., sequences for the amino-terminal translation initiating methionine and the subsequent 7 residues of beta-galactosidase producing a catalytically active beta galactosidase fusion protein in which the amino-terminal methionine is ligated in frame with a histidine tag; and the like.

Similarly, in yeast, such as Saccharomyces cerevisiae, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

A host cell is optionally chosen for its ability to modulate the expression of the inserted sequences or to process the expressed protein in the desired fashion. Such modifications of the protein include, but are not limited to, glycosylation, acetylation, carboxylation, phosphorylation, lipidation, acylation etc. Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant neuregulin polypeptide, stable expression systems are typically used. For example, polynucleotides encoding a neuregulin polypeptides are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a neuregulin polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means and the resulting crude extract retained for further purification. Eukaryotic or microbial cells employed in expression of proteins can be disrupted by any convenient method, including freeze-thaw cycling, sonication, mechanical disruption or use of cell lysing agents or other methods, which are well know to those skilled in the art.

Expressed neuregulin polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography and lectin chromatography. Protein refolding steps can be used, as desired, in completing configuration of the mature protein. Finally, high performance liquid chromatography (HPLC) can be employed in the final purification steps.

In certain examples, the nucleic acids are introduced into vectors suitable for introduction and expression in prokaryotic cells, e.g., *E. coli* cells. For example, a nucleic acid including a polynucleotide sequence that encodes a F2GF1 chimeric RSV antigen can be introduced into any of a variety of commercially available or proprietary vectors, such as the pET series of expression vectors (e.g., pET19b and pET21d). Expression of the coding sequence is inducible by IPTG, resulting in high levels of protein expression. The polynucleotide sequence encoding the chimeric RSV antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode F2GF 1 chimeric RSV antigens.

In another example, a polynucleotide sequence that encodes a neuregulin is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the neuregulin is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the neuregulin is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the SF9 and the High Five (Hi5) cell line derived from a cabbage looper, *Trichoplusia ni.*

Following transfection and induction of expression (according to the selected promoter and/or enhancers or other regulatory elements), the expressed polypeptides are recovered (e.g., purified or enriched) and renatured to ensure folding into a biologically active conformation.

In yet other embodiments, the neuregulins are expressed in vivo using viral or non-viral expression vectors.

Viral-Based Expression Vectors.

In some embodiments, neuregulin or siRNA encoding sequences (or shRNAs) are delivered from viral-derived expression vectors. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers and can be delivered in aerosol formulation and can transfect non-dividing cells. Poxyiral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

Non-Viral Expression Vectors.

In other embodiments, nonviral delivery systems are utilized for delivery of plasmid vectors or other bioactive non nucleic acid agents using lipid formulations comprising, for example, liposomes, such as cationic liposomes (e.g., DOTMA, DOPE, DC-cholesterol) and anionic liposomes. Liposomes can be further conjugated to one or more proteins or peptides to facilitate targeting to a particular cell, if desired. Administration of a composition comprising a compound and a cationic liposome can be administered to the blood afferent to a target organ or inhaled into the respiratory tract to target cells of the respiratory tract. Furthermore, active agent(s) can be administered as a component of a microcapsule or nanoparticle that can be targeted to a cell type of interest using targeting moieties described herein or that can be designed for slow release of one or more active agent(s) in accordance with a predetermined rate of release or dosage.

In other embodiments, the nucleic acids may be delivered in vivo by electroporation, the technology for which is available from Genetronics, Inc. (San Diego, Calif.), as well as by means of a SONOPORATION machine (ImaRx Pharmaceutical Corp., Tucson, Ariz.).

The nucleic acids may be in solution or suspension (for example, incorporated into microparticles, liposomes or cells). These may be targeted to a particular cell type via antibodies, receptors or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted and then either recycle to the cell surface, become stored intracellularly or are degraded in lysosomes. The internalization pathways serve a variety of functions, such as nutrient uptake, removal of activated proteins, clearance of macromolecules, opportunistic entry of viruses and toxins, dissociation and degradation of ligand and receptor level regulation. Many receptors follow more than one intracellular pathway, depending on the cell type, receptor concentration, type of ligand, ligand valency and ligand concentration.

The present invention is further illustrated by the following examples that should not be construed as limiting. The contents of all references, patents and published patent applications cited throughout this application, as well as the Figures and Tables, are incorporated herein by reference.

Example 1

Figure 1V:
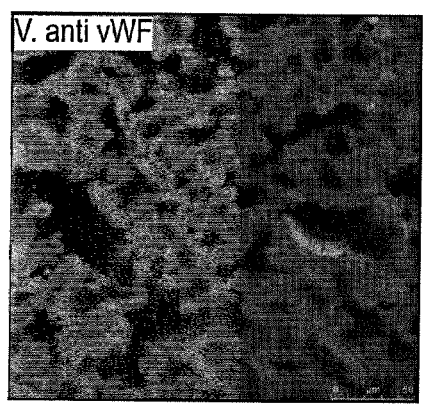
Figure 1W:
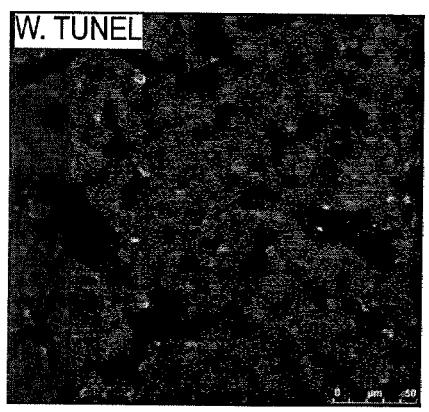
Figure 1X:
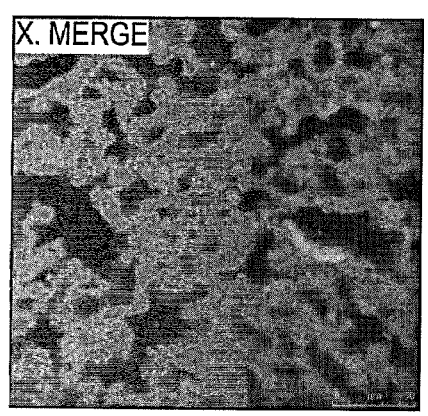

Role of Neuregulin-1 in Cerebral Malaria Pathogenesis 1.1. Infection of C57BL/6 Mice with *P. berghei* ANKH (PBA) Causes Brain, Lung and Kidney Damage C57BL/6 mice were intraperitoneally inoculated with $1 \times 10^6$ *P. berghei* parasitized RBC (pRBC or iRBC) (C=non-infected control, In=infected with PBA). Parasitemias in both WT and CXCL10-/- mice were below 15% after infection with PBA for 8 days (A). Hb levels were lower in infected WT mice compared to non-infected controls, but at similar levels in CXCL10-/- mice compared to corresponding non-infected controls (B). Similar maturation stages of the parasite were observed in WT and CXCL10-/- mice blood smear (C and D). Brains of ECM animals showed disruption of vessel walls with endothelial degeneration and cerebral edema as indicated by enlargement of perivascular spaces (1F). Parenchymal microhemorrhages (1G and 1H, yellow arrows) were common in white and grey matter in ECM mice. Adherence of pRBC and leucocytes to brain vessels and vascular plugging were present in all sections of ECM mice analyzed (1H, black arrow). Histopathological examination also showed necrotic findings in grey matter in PBA-infected C57BL16 mice (1 H, yellow arrow head). No histological lesions were detected in non-infected controls of brain tissues (1 E). In the lung of C57BL16 mice, the onset of ECM was characterized by the presence of leukocyte infiltrates and alveolar edema without marked thickening of the alveolar septum by HE staining (1 L) compared to normal control (1 K). Apoptotic cells were revealed by TUNEL assay (1T, in red). The low-power images (1S) show strong vWF immunoreactivity in pulmonary tissues and blood vessels. Co-localization of vWF-positive and TUNEL-positive cells (1U) in lung confirmed the presence of apoptotic pulmonary endothelial cells. FIGS. 1V, 1W and 1X showed no apoptotic pulmonary endothelial cells in non-infected control animals. Kidney histopathology revealed that infection of C57BL16 with *P. berghei* caused proximal convoluted tubular cell swelling and denaturation. The onset of ECM was characterized by proximal convoluted tubular cell swelling and eosinophilic denaturation, as well as narrowed space between tubules (1 P) compared to non-infected control (1O). No obvious pathological lesions were detected in CXCL10 gene deficient mice (CXCL10-/-) infected with PBA in brain (1J vs. 1I), lung (1M vs. 1N) and kidney (1Q vs. 1R) compared to corresponding controls.

1.2. HEME/HO-1, CXCL10 and STAT3 Mediate PBA ECM.

Figure 3:
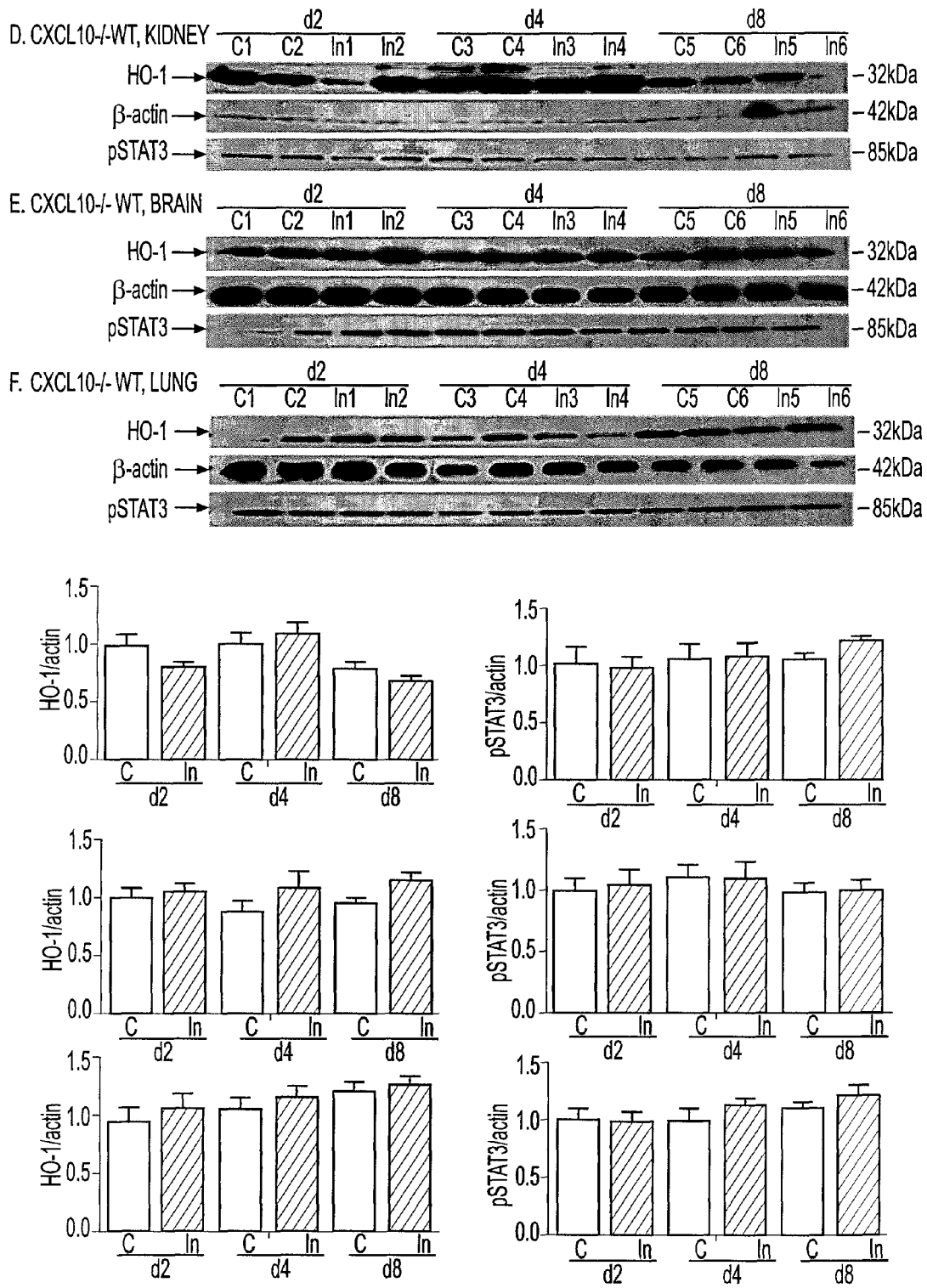
FIG. 3 shows expression of HO-1 and pSTAT3 in kidney (A, D), brain (B, E) and lung (C, F) in C57BL/6 WT (A-C) and CXCL10 deficient (CXCL10-/-) (D-F) mice infected with PBA.
Figure 4:
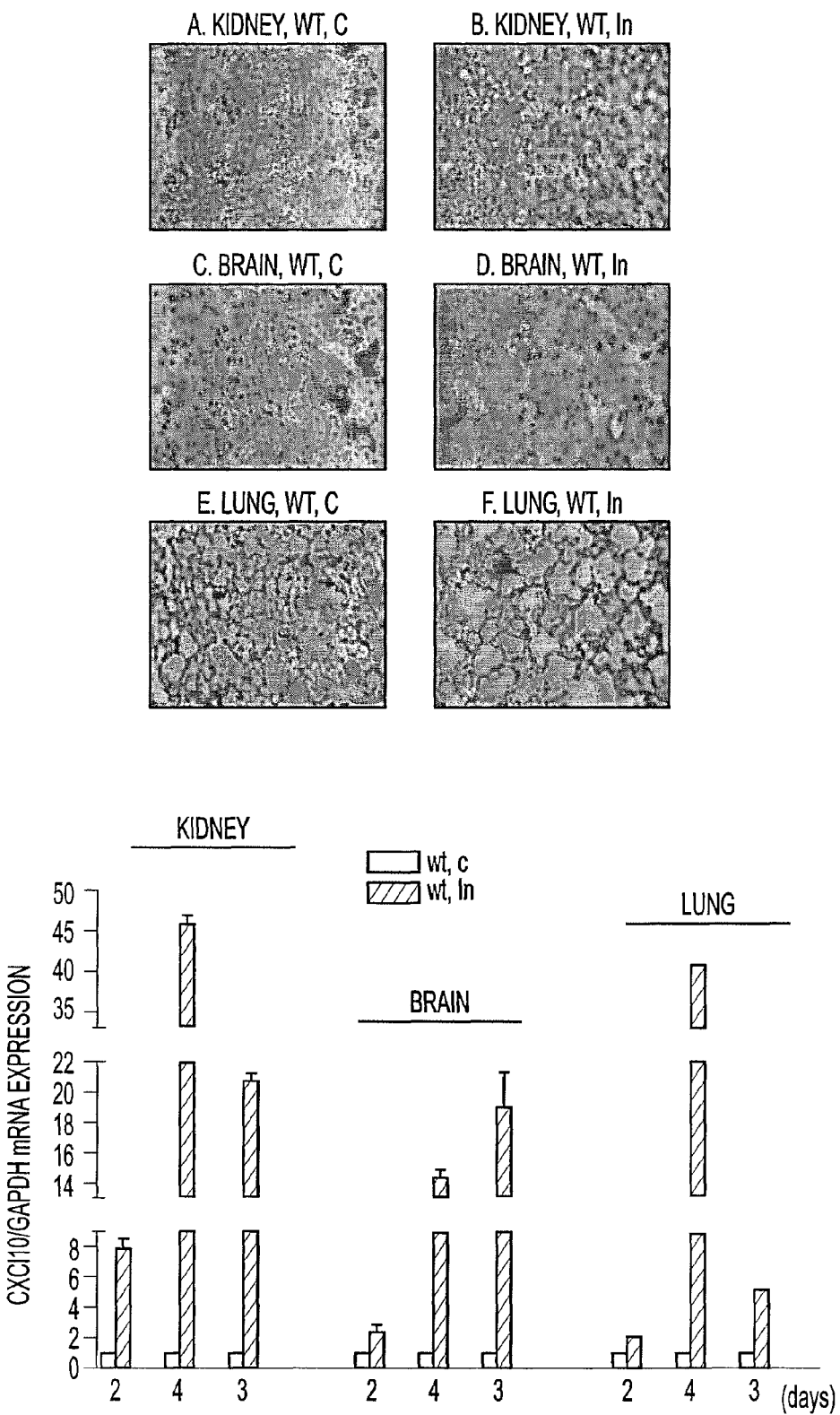
FIG. 4 shows CXCL10 gene expression in kidney (A, B), brain (C, D) and lung (E, F) tissues of C57BL/6 control mice (A, C, E) and C57BL/6 mice infected with PBA (B, D, F).

Plasma levels of HEME significantly increased in infected wild type (WT) C57 BL/6 mice than those of non-infected controls, indicating that plasma HEME is associated with PBA infection in mice (data not shown). Additionally, HO-1 plasma levels were significantly higher in the infected wild type C57 BL/6 mice compared to the control mice, suggesting HO-1 could be a protective factor against HEME (data not shown). CXCL10-/- infected mice showed the same pattern as CXCL10-/- non-infected mice regarding plasma concentration of HEME and HO-1. When infected with PBA, CXCL10-/- mice do not present the same increase in the levels of HEME or HO-1 as WT mice do during infection (data not shown). FIG. 3 shows the mean ratio of HO-1 mRNA expression to GAPDH expression (n=6) in mice on day 2, 4 and 8 post infection respectively. Infection of C57BL/6 WT or CXCL10-/- mice with PBA (In=infection, c=control) up regulated HO-1 mRNA in the kidney (A), brain (B) and lung (C), suggesting HO-1 expression may be protective against *P. berghei* induced damage. Mice deficient in CXCL10 (CXCL10-/-) down regulated HO-1 in both uninfected and infected C57BL/6 mice (white vs. red; black vs. yellow), suggesting that transcription of mouse HO-1 gene is positively regulated by CXCL10. HO-1 and the active STAT3 molecule-phosphorylated STAT3 (pSTAT3Tyr705) protein, was examined in kidney (FIG. 3A), brain (FIG. 3B) and lung (FIG. 3C) of mice. The data showed that PBA infection up regulates HO-1, pSTAT3 protein in various tissues of C57BL/6 mice. The levels of pSTAT3 which peaked on day 2 in kidney and lung, on day 4 in brain, appeared earlier than those of HO-1, which peaked on day 4 in kidney and lung, on day 8 in brain respectively. However, PBA infection did not up regulate HO-1 protein in CXCL10-/- mice (FIG. 3 D-F). FIG. 4 shows that CXCL10 mRNA expression is higher in kidney, brain and lung tissues in infected than uninfected mice on day 4 and day 8 respectively. The similar results were further confirmed by immunohistochemistry analysis as shown in the right panel of FIG. 4. The membrane and cytoplasm staining of CXCL10 protein were much stronger in the kidney, brain and lung of PBA infected WT C57 BL/6 mice compared to corresponding controls (FIG. 4B vs. 4A, 4D vs. 4C, 4F vs. 4E). These data indicate that fatal ECM is associated with high levels of CXCL10 expression in vital organs in C57BL/6 WT mice.

1.3. Neuregulin-1 (NRG-1) Treatment Attenuates CXCL10- and HEME-Mediated Mortality in Experimental Cerebral Malaria (ECM).

Figure 5C:
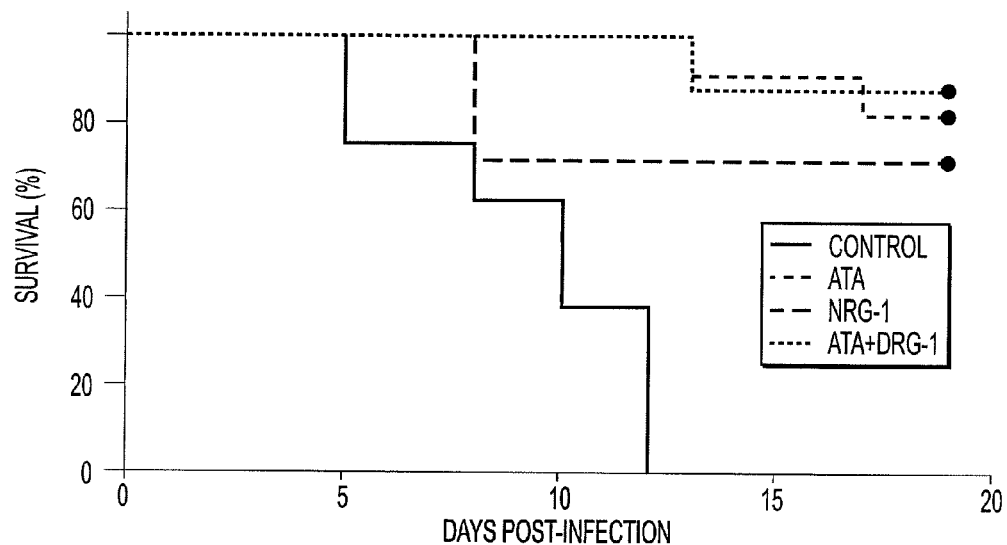
FIG. 5C shows the efficacy of NRG-1 administration in combination with the antimalarial drug, artemether (ATA). Female C57Bl/6 mice infected with PBA were treated from day 6 to 9 with NRG-1, ATA, NRG-1+ATA or untreated (control).
Figure 5D:
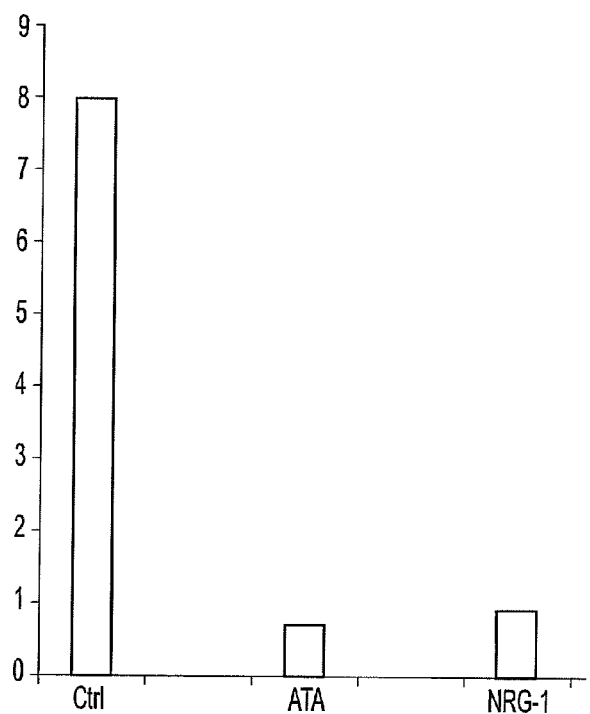
FIG. 5D shows downregulation of serum CXCL10 levels following treatment with ATA or NRG-1.

NRG-1 mRNA and protein were significantly increased in PBA infected mice and human CM patients (FIG. 5A, 5B) (NM: no Malaria; SMA: severe anemia malaria). The efficacy of NRG-1 combination therapy on CM outcomes was determined in ECM. Female C57Bl/6 mice treated with NRG-1 after infected with PBA (ip) from day 6 to 9. NRG-1 therapy (FIG. 5C) significantly extended survival of CBA/J mice infected with *Plasmodium berghei* ANKA when compared to controls (p value=0.035). This study also revealed upregulation of certain NRG-1 isoforms as a host response during the pathogenesis of CM. However, the levels of parasites in the mice did not change after NRG-1 treatment. These results suggest that exogenously administering specific isoforms of NRG-1 can effectively prevent or reduce severity of CM and fatal disease.

1.4. HO-1 and CXCL10 are Upregulated and STAT3 is Activated by HEME in CRL-2581 Cells.

High level of free HEME produced during malaria infection causes inflammation that damages host vascular endothelium and is a major contributor to pathogenesis of severe malaria. To determine how HEME stimulates HO-1, CXCL10 and STAT3 signaling pathways in vitro, mouse brain endothelial cell line CRL2581 was treated with HEME and the effects of HEME on expression of HO-1, CXCL10 and STAT3 activation was assessed. The results show that expression of HO-1 mRNA and protein (data not shown) were significantly up regulated by HEME and HO-1 enzymatic inducer-CoPP treatment; were down regulated by HO-1 enzymatic activity inhibitor-ZnPP (data not shown). The expression of CXCL10 mRNA was also significantly up regulated by HEME. HEME enhances CXCL10 promoter activity in a dose-dependent manner (data not shown). pSTAT3 was increased by HEME from 1 μM and peaked at 5 μM and then decreased (FIG. 6A). When pSTAT3 was reduced by short interfering STAT3 (siSTAT3) (FIG. 6B) or pharmacological inhibitor of Jak, AG490 (FIG. 6C), HO-1 protein expression was inhibited correspondingly. These data indicated that HEME induced production of HO-1 by way of STAT3 signaling pathway. Reduced activation of STAT3 caused by siSTAT3 (FIG. 6D) and AG490 (FIG. 6E) also caused reduced expression of CXCL10. In addition, when CXCL10 was blocked by anti-CXCL10 antibody, HO-1 induction by HEME was decreased to one half, indicating that CXCL10 directly induces HO-1 expression (FIG. 6F). Interestingly, pSTAT3 level was increased by CoPP and decreased by ZnPP (FIG. 5G), which indicates that HO-1 also regulates STAT3 signaling.

1.5. Protective Effect of JAK2/STAT3 Inhibition on Human Brain Microvascular Endothelial Cell (HBVEC) Death.

Figure 7:
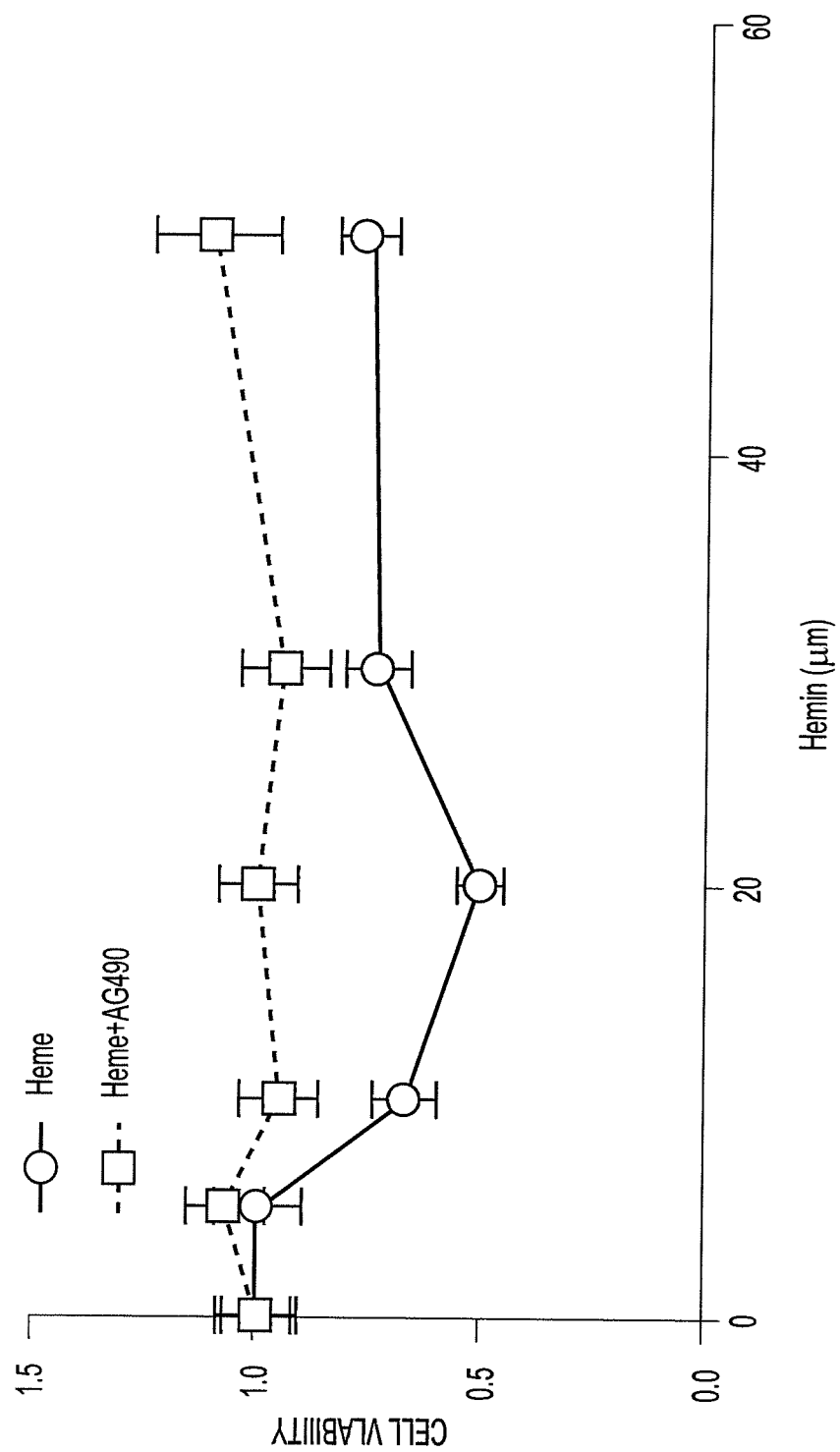
FIG. 7 shows protection against cell death by inhibition of the JAK2/STAT3 signalling pathway. Human brain microvascular endothelial cells (HBVEC) were treated with HEME or with HEME plus AG490 and monitored for cell death progression by MTT assay.

Cell death progression in HBVEC cultured after treatment with HEME or HEME+AG490 (50 μmol/l) for 24 h as assayed by MTT assay (*P<0.05, n=3 triplicate experiments). The curves correspond to 3 experiments run in parallel. In all the samples, the same concentration of vehicle (DMSO, 0.1%) was used. AG490 can rescue the HEME-induced apoptosis in HBVEC (FIG. 7).

1.6. Analysis of Human JAK/STAT Signaling Pathway Using Real Time $RT^2$ Profile PCR Arrays.

Target genes of JAK/STAT3 signaling pathway upon HEME treatment was further assessed using real time $RT^2$ Profile PCR arrays (Qiagen, PAHS-039A). The results shown in FIG. 7 are expressed as the fold changes in expression obtained by comparing HBVEC treated with 20 μM HEME or with vehicle as control. FIG. 8 is a list of up regulated and down regulated genes with fold-change greater than 2. The up regulated genes include STAT-induced gene matrix metallopeptidase 3 (MMP3), apoptosis-related gene CCAAT/enhancer binding protein (C/EBPb), Fc fragment of IgG, high affinity Ia, receptor (FCGR1A), Jun B proto-oncogene (JUNB), nuclear factor of kappa light polypeptide gene enhancer in B-cells 1 (NFκB), suppressor of cytokine signaling (SOCS3), SOCS4 and signal transducer and activator of transcription 4 (STAT4). The down regulated genes consist of coagulation factor II receptor (F2R) and 2'-5'-oligoadenylate synthetase 1 (OAS1).

1.7. Summary of Results

These data not only confirmed that infection of C57BL/6 mice with PBA results in significant brain tissue damage, but demonstrate that (1) STAT3 is activated by *P. berghei* ANKA (PBA) infection in vivo and HEME in vitro; (2) HEME upregulates HO-1 and CXCL10 production through the STAT3 pathway and regulates CXCL10 at the transcriptional level in vitro. The target genes of STAT3, such as MMP3 and C/EBPb, which are related to programmed cell death (PCD; apoptosis), are upregulated; (3) HO-1 transcription is positively regulated by CXCL10; (4) HO-1 regulates STAT3 signaling; (5) NRG-1 is up regulated in mouse CM model and human cerebral malaria patients; and (6) NRG-1 attenuates mice mortality in experimental cerebral malaria. Thus, HEME-CXCL10-STAT3 systems during *Plasmodium* infection are central to the pathogenesis of fatal CM and NRG-1 and present potential targets for neuroprotective intervention for cerebral malaria by altering the signaling pathways thereof.

Example 2

Neuregulin-1 Regulates Macrophage Inflammatory Phenotype

Previously, the effect of NRG-1 on gene expression in activated macrophages using cultures of human U937 monocytic cells activated by incubation with PMA and LPS was examined (Xu et al., 2005). In these studies, cultures were treated for 24 hours with plating medium or PMAILPS±NRG-1. The results of these studies evaluated the expression of COX-2 mRNA in macrophage cultures by R I PCR and showed relatively low basal levels of COX-2 mRNA, which were induced following stimulation of cells with PMAILPS for 24 hours, the induction of which was attenuated by NRG-1. Based on the combined in vitro and in vivo data, it was hypothesized that NRG-1 can block neuronal damage and damage caused by pathogens by shifting the immune state to baseline in the presence of a pro-inflammatory challenge.

Immune cells can transform into different phenotypes in the presence of specific stimuli. Immune cell phenotypes have best been described for T-helper cells. Classically activated T cells induced by pro-inflammatory stimuli are known as Th1 cells. Alternatively, activated T cells produced in the presence of anti-inflammatory stimuli are known as Th2 cells. Other T-helper cell phenotypes involved in the immune response include Th17, Th9 and Treg cells. Similarly, macrophages have M1 (classically activated) and M2 (alternatively activated) phenotypes that are related to T cell phenotypes. To examine the effect of the NRG-1 on macrophage phenotype, a Luminex multiplex immunoassay measuring twenty cytokines in a single well was performed. Table 1 shows that incubation of human Thp-1 monocytes with interferon gamma and LPS resulted in the induction of a massive M1-type response characterized by increases in M1 cytokines and chemokines, such as IL-1, IL-6, TNF alpha and others (Table 1). Treatment with NRG-1 and had no effect alone, but completely blocked the induction of all M1 cytokines and chemokines in the above-described assay (Table 1). The M2 cytokines IL-10 slightly increased following NRG-1 treatment (Table 1). These results demonstrate that NRG-1 shifts macrophages away from the M1 phenotype towards an M2 phenotype, perhaps though novel mechanisms.

TABLE 1

| | | | Cytokine concentrations from Luminex multiplex immunoassay | | | | | | | |
|---|---|---|---|---|---|---|---|---|---|---|
| Type | Well | Treatment | IFN-γ | IL-10 (CSIF) | IL-12 (p70) | IL-17A (CTLA8) | IL-1B | TNF-α | IL-6 | IL-4 | IL-2 |
| X1 | A3, A4 | Control | *0.40 | *0.31 | *1.16 | *0.75 | *0.63 | *0.74 | *0.30 | OOR< | *0.49 |
| X5 | E3, E4 | NRG-1 | *0.29 | *0.37 | *1.28 | *0.63 | *0.69 | *1.09 | *0.56 | OOR< | *0.55 |

TABLE 1-continued

Cytokine concentrations from Luminex multiplex immunoassay

| Type | Well | Treatment | IFN-γ | IL-10 (CSIF) | IL-12 (p70) | IL-17A (CTLA8) | IL-1B | TNF-α | IL-6 | IL-4 | IL-2 |
|---|---|---|---|---|---|---|---|---|---|---|---|
| X10 | C5, C6 | LPS + IFN-γ | 298.23 | 6.42 | 11.85 | 15.15 | 101.53 | 3437.6 | 3361.2 | 4.18 | 1.21 |
| X9 | B5, B6 | LPS + IFNγ + NRG-1 | 6.95 | 8.65 | 6.5 | 13.31 | 26.57 | 1661.7 | 21.51 | *2.88 | *0.94 |

Concentration units = pg/ml
*Value extrapolated beyond standard range
OOR< = Out of range below The above description is for the purpose of teaching the person of ordinary skill in the art how to practice the present invention and is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the components and steps in any sequence that is effective to meet the objectives there intended, unless the context specifically indicates the contrary. All the references cited in the specification are herein incorporated by reference in their entirety.

What is claimed is:

1. A method for inhibiting tissue damage caused by malaria in a subject, comprising:
administering to a subject in need of such treatment a composition comprising a therapeutically effective amount of a neuregulin-1, wherein said neuregulin-1 is administered in a dosage range from about 0.01 mg/kg body weight/day to about 1000 mg/kg body weight/day.

2. The method of claim 1, wherein said neuregulin-1 is administered in conjunction with a secondary agent against malaria.

3. The method of claim 2, wherein the secondary agent is a HEME neutralization agent, a CXCL10 inhibitor, a CXCR3 inhibitor, a STAT3 inhibitor, an anti-inflammatory agent, an antimalarial agent or combination thereof.

4. The method of claim 3, wherein the secondary agent comprises an anti-CXCL10 antibody, an anti-CXCR3 antibody, an anti-STAT3 antibody or an anti-HEME antibody.

5. The method of claim 2, wherein the secondary agent is a HEME neutralization agent.

6. The method of claim 1, wherein the tissue damage comprises secondary damage induced by an inflammatory response.

7. The method of claim 6, wherein said secondary damage induced by an inflammatory response comprises damage to a system selected from the group consisting of the urogenital system, nervous system, digestive system, respiratory system, skin and cardiovascular system.

8. The method of claim 1, wherein said tissue damage is brain damage.

9. A method for inhibiting secondary tissue damage caused by malaria in a subject, comprising:
administering into a subject in need of such treatment an effective mount of a neuregulin-1.

10. The method of claim 9, further comprising:
administering into said subject a secondary agent selected from the group consisting of HEME neutralization agent, CXCL10 inhibitor, CXCR3 inhibitor, STAT3 inhibitor, anti-inflammatory agent, antimalarial agent and combinations thereof.

11. A method for reducing mortality caused by the secondary effect of malaria in a subject, comprising:
administering into a subject in need of such treatment an effective amount of neuregulin-1.

12. The method of claim 11, further comprising:
administering into said subject a secondary active agent selected from the group consisting of HEME neutralization agent, CXCL10 inhibitor, CXCR3 inhibitor, STAT3 inhibitor, anti-inflammatory agent, antimalarial agent and combinations thereof.

* * * * *